(12) United States Patent
Boyle et al.

(10) Patent No.: US 9,459,253 B2
(45) Date of Patent: Oct. 4, 2016

(54) ASSAY FOR MEASURING CELL-MEDIATED IMMUNORESPONSIVENESS

(75) Inventors: Jeff Boyle, Pearcedale (AU); Rachel De Las Heras, Belgrave (AU)

(73) Assignee: Cellestis Limited, Chadstone (AU)

( * ) Notice: Subject to any disclaimer, the term of this patent is extended or adjusted under 35 U.S.C. 154(b) by 469 days.

(21) Appl. No.: 13/516,150

(22) PCT Filed: Dec. 21, 2010

(86) PCT No.: PCT/AU2010/001717
§ 371 (c)(1),
(2), (4) Date: Aug. 21, 2012

(87) PCT Pub. No.: WO2011/075773
PCT Pub. Date: Jun. 30, 2011

(65) Prior Publication Data
US 2013/0034844 A1    Feb. 7, 2013

Related U.S. Application Data

(60) Provisional application No. 61/289,880, filed on Dec. 23, 2009.

(51) Int. Cl.
| *A61K 38/00* | (2006.01) |
| *C12N 5/00* | (2006.01) |
| *C12N 5/02* | (2006.01) |
| *G01N 33/569* | (2006.01) |
| *G01N 33/50* | (2006.01) |

(52) U.S. Cl.
CPC .... *G01N 33/56972* (2013.01); *G01N 33/5047* (2013.01)

(58) Field of Classification Search
None
See application file for complete search history.

(56) References Cited

U.S. PATENT DOCUMENTS

| 4,016,043 A | 4/1977 | Schuurs et al. |
| 4,018,653 A | 4/1977 | Mennen |
| 4,424,279 A | 1/1984 | Bohn et al. |
| 2003/0199006 A1 | 10/2003 | Britz et al. |

FOREIGN PATENT DOCUMENTS

| WO | 2005/118629 A1 | 12/2005 |
| WO | 2010/009494 A1 | 1/2010 |

OTHER PUBLICATIONS

Hansson et al., Stem Cells, 2007, V.25, pp. 1507-1510.*
Groth et al.. "T cell activation: in vivo veritas" Immunology and Cell Biology 2004, 82: 260-268 teach.*
Bigos et al., "Nine Color Eleven Parameter Immunophenotyping Using Three Laser Flow Cytometry," *Cytometry* 36:36-45, 1999.
Chang et al., "Impaired Quality of the Hepatitis B Virus (HBV)-Specific T-Cell Response in Human Immunodeficiency Virus Type 1-HBV Coinfection," *Journal of Virology* 83(15):7649-7658, Aug. 2009.
Cooper et al., "Immunodeficiency Disorders," *American Society of Hematology*:314-330, 2003.
Daneshvar et al., "Detection of biomolecules in the near-infrared spectral region via a fiber-optic immunosensor," *Journal of Immunological Methods* 226:119-128, 1999.
Deetz et al., "Gamma Interferon Secretion by Human Vγ2Vδ2 T Cells after Stimulation with Antibody against the T-Cell Receptor plus the Toll-Like Receptor 2 Agonist $Pam_3Cys$," *Infection and Immunity* 74(8):4505-4511, Aug. 2006.
Douek et al., "Immunopathogenesis of AIDS," *Annual Review of Medicine* 60:471-484, 2009.
Durig et al., "Fourier Transform Raman Spectroscopy of Brightly Colored Commercially Available Dyestuffs and Pigments," *Journal of Raman Spectroscopy* 24:281-285, 1993.
Eriksson et al., "Lipid and water diffusion in bicontinuous cubic phases measured by NMR," *Biophysical Journal* 64:129-136, Jan. 1993.
Fu et al., "A microfabricated fluorescence-activated cell sorter," *Nature Biotechnology* 17:1109-1111, Nov. 1999.
Hengel et al., "Surrogate Markers of Immune Function in Human Immunodeficiency Virus-Infected Patients: What Are They Surrogates for?," *The Journal of Infectious Diseases* 188:1791-1793, Dec. 15, 2003.
Hu et al., "New approaches to treatment of primary immunodeficiencies: fixing mutations with chemicals," *Current Opinion in Allergy & Clinical Immunology* 8(6):540-546, Dec. 2008.
Kowalski et al., "Immunodiagnostics: Evaluation of Functional T-Cell Immunocompetence in Whole Blood Independent of Circulating Cell Numbers," *Journal of Immunotoxicology* 4:225-232, 2007.
Lakowicz et al., "Time-Resolved Fluorescence Spectroscopy and Imaging of DNA Labeled with DAPI and Hoechst 33342 Using Three-Photon Excitation," *Biophysical Journal* 72:567-578, Feb. 1997.
Lewis et al., "Erratum to "The use of Fourier Transform Infrared (FT-IR) spectroscopy to study the state of heterobifunctional reactive dyes"," *Dyes and Pigments* 42:197, 1999.
Llewellyn-Smith et al., "Effects of anti-CD4 antibody treatment on lymphocyte subsets and stimulated tumor necrosis factor alpha production: A study of 29 multiple sclerosis patients entered into a clinical trial of cM-T412," *Neurology* 48:810-816, 1997.
Matesanz et al., "Global Observatory and Database on Donation and Transplantation: World Overview on Transplantation Activities," *Transplantation Proceedings* 41:2297-2301, 2009.
Nowroozalizadeh et al., "Studies on toll-like receptor stimuli responsiveness in HIV-1 and HIV-2 infections," *Cytokine* 46:325-331, 2009.

(Continued)

*Primary Examiner* — Michail Belyavskyi
(74) *Attorney, Agent, or Firm* — Seed IP Law Group PLLC

(57) ABSTRACT

The present invention relates generally to the field of immunological-based diagnostic assays. More particularly, the present invention contemplates a method for measuring cell-mediated immunoresponsiveness. The present invention further enables determination of the immunosuppressive effects of disease conditions, therapeutic agents and environmental contaminants. The assay of the present invention is also capable of integration into pathology architecture to provide a diagnostic reporting system and to facilitate point of care clinical management.

25 Claims, 11 Drawing Sheets

(56) References Cited

OTHER PUBLICATIONS

Oquendo et al., "Suppressive effect of hepatitis B virus on the induction of interlueukin-1 beta and interleukin-6 gene expression in the THP-1 human monocytic cell line," *European Cytokine Network* 7(4):793-800, 1996. (Abstract Only).

Rahman et al., "Infrared and Raman Spectra of a Single Resin Bead for Analysis of Solid-Phase Reactions and Use in Encoding Combinatorial Libraries," *The Journal of Organic Chemistry 63*: 6196-6199, 1998.

Rapaport et al., "Visible light emission from dyes excited by simultaneous absorption of two different frequency beams of light," *Applied Physics Letters* 74(3):329-331, Jan. 18, 1999.

Schrem et al., "Aftercare for Patients With Transplanted Organs," *Deutsches Ärzteblatt International* 106(9):148-156, 2009.

Solomon et al , "Immunological and Virological Failure after Antiretroviral Therapy is Associated with Enhanced Peripheral and Thymic Pathogenicity," *The Journal of Infectious Diseases 187*: 1915-1923, Jun. 15, 2003.

Tawa et al., "Polarized Light-Induced Anisotropy in Polymer Films Doped with Az Dyes in the Photostationary State Studied by IR Spectroscopy," *Materials Research Society Symposium Proceedings 488*:885-890, 1998.

Youvan et al., "Calibration of Fluorescence Resonance Energy Transfer in Microscopy Using Genetically Engineered GFP Derivatives on Nickel Chelating Beads," *Biotechnology* 3:1-18, 1997.

* cited by examiner

ASSAY FOR MEASURING CELL-MEDIATED IMMUNORESPONSIVENESS

This application is associated with and claims priority from U.S. Provisional Patent Application No. 61/289,880, filed on 23 Dec., 2009, entitled "An Assay", the entire contents of which, are incorporated herein by reference.

FIELD

The present invention relates generally to the field of immunological-based diagnostic assays. More particularly, the present invention contemplates a method for measuring cell-mediated immunoresponsiveness. The present invention further enables determination of the immunosuppressive effects of disease conditions, therapeutic agents and environmental contaminants. The assay of the present invention is also capable of integration into pathology architecture to provide a diagnostic reporting system and to facilitate point of care clinical management.

BACKGROUND

Bibliographic details of the publications referred to by author in this specification are collected alphabetically at the end of the description.

Reference to any prior an in this specification is not, and should not be taken as, an acknowledgment or any form of suggestion that this prior art forms part of the common general knowledge in any country.

Immunological-based diagnostics provides an important tool in detecting a variety of disease conditions. This is especially the case given the specificity of components within the immune system. Notwithstanding this specificity, immunological-based diagnostics are not necessarily always sensitive enough to detect low levels of adaptive and/or innate immune activity, such as in response to a low grade infection or in the presence of a persistent low level infection or in subjects exhibiting immunodeficiency or any form of immunosuppression. There is a need to develop diagnostic assays with enhanced sensitivity in relation to cell-mediated immunoresponsiveness due to adaptive and innate immune potential. This is particularly the case in subjects exposed to or exhibiting disease conditions and agents which induce or are associated with immunosuppression.

One form of immunological-based diagnostic assays involves the stimulation of T-cells with antigens or mitogens in either isolated cell culture or whole blood culture followed by the detection of effector molecules such as cytokines produced by the activated T-cells (also referred to as effector T-cells). The effector molecules are generally detected using techniques such as enzyme immunoassays, multiplex bead analysis, ELISpot and flow cytometry. Such assays are useful for detecting disease-specific T-cell responses.

The ability to assess cell-mediated immune responsiveness of a subject is particularly important in managing immunodeficiency and immunosuppression. Immunodeficiency is characterized by a reduced ability to effectively mount an immune response This compromized or absent response can result from a primary or acquired (secondary) immunodeficiency.

Primary immunodeficiencies (PIDs) are genetically inherited and characterized by deficiencies of distinct components of the adaptive or innate immune system (Hu and Gatti, *Curr Opin Allergy Clin Immunol.* 8(6):540-546, 2008). Nonetheless, most immunodeficiencies are acquired (secondary) and can be induced by a pathogenic agent, as occurs with HIV infection; induced by drugs, as in immunosuppressive treatment following organ transplantation; induced by disease conditions, as can occur in cancer (e.g. leukemia, lymphoma); or induced by environmental contaminants and pollutants.

The molecular basis of immunodeficiency is diverse, however, cell-mediated immunity plays a key role in mediating many of the observed clinical manifestations. At present, immunodeficiency syndromes are diagnosed and managed in an ad hoc manner depending on the causal agent.

For example, the primary hallmark of HIV infection is progressive loss of $CD4^+$ T-cells and impaired global immune function including an impaired antigen-specific adaptive immune response to pathogens such as cytomegalovirus (CMV) and Hepatitis B virus (HBV) [Douek et al, *Annu. Rev. Med.* 60:471-84, 2009 and Chang et al, *J. Virol.* 83:7649-58, 2009]. Hence, $CD4^+$ T-cell count and viral load remain the key surrogate markers of HIV infection and have been extensively validated as predictive of both immune dysfunction and with progressive infection and immune reconstitution following prophylaxis (Hengel and Kovacs, *J. Infect. Dis.* 188(12):1791-3, 2003). However, many instances exist in which clinical disease does not correlate with the level of immune function as predicted by these surrogate markers particularly when opportunistic infections develop in the presence of normal $CD4^+$ T-cell counts and low viral loads (Solomon et al, *J. Infect. Dis.* 187:1915-23, 2003).

Similarly, monitoring the cellular immunodeficiency status of patients that have undergone solid organ transplants (SOTs) and are receiving medications to suppress their immune system (immunosuppressants) as an anti-rejection measure, are also managed in an ad hoc manner. Typically, patient immunosuppressant drug levels are monitored as are regular blood counts and incidence of graft, nosocomial or community-acquired infections (Schrem et al, *Dtsch Arztebl Int.* 106(9):148-156, 2009).

The inherent problem associated with many of the current markers used to monitor and define immunodeficiency associated with disease states is the absence of cell-mediated immunity. A number of T-cell function tests have been developed that measure lymphoproliferative responses to mitogens such as phytohemagglutinin (PHA), pokeweed mitogen and concanavalinA (ConA). However, these only measure the functional ability of T-cells; a subset of cells involved in cell-mediated immunity. Importantly, it has become increasingly evident that innate immune mechanisms contribute greatly to host defence, either through acting alone or by enhancing specific T-cell responses (Cooper et al, *Hematology:*314-30, 2003). Therefore, the functional responses of innate (natural killer [NK] cell) and adaptive (T-cell) immune cells together form a more comprehensive analysis of cell-mediated immunity.

The ability to assess cell-mediated immunity is of clinical importance. For example, in excess of 33 million adults and children are infected with HIV (2008 Report on the Global AIDS Epidemic, UNAIDS; ISBN 978 92 9 173711 6) and currently around 100,000 solid organ transplantations are performed per year worldwide (Matesanz et al, *Transplant Proc.* 41(6):2297-301, 2009).

Innate immune dysregulation has been implicated in HIV infection with a whole blood IFN-γ assay described for the monitoring of innate immune responsiveness to the TLR-7/8 agonist compound (a imidazoquinoline compound, 8848) [Nowroozalizadeh et al, *Cytokine* 46:325-31, 2009]. Furthermore, a diagnostic device that measures functional T-cell responses (Cylex ImmuKnow (Registered Trade Mark), as described in US 2003/0199006 A 1) measures ATP production from PHA-stimulated $CD4^+$ cells (Kowalski et al, *J Immunotoxicol.* 4(3):225-32, 2007). Specifically, the Cylex assay has demonstrated clinical utility in the SOT setting such that adverse events including infection and rejection can be adequately managed.

There is a need to develop an assay which can assess the combined functional status of innate and adaptive cell-mediated immunoresponsiveness in a subject and to determine disease conditions and agents which induce immunosuppression.

SUMMARY

The present invention provides a method for assessing the status and potential of cell-mediated immunity in a subject. The method contemplated herein is predicated in part on the co-stimulation of adaptive and innate immune responses. This provides a predictive measure of cell-mediated immunity potential including the extent of any immunosuppression in a target subject. In an embodiment, cells in whole blood or a fraction thereof are contacted with one or more agents which stimulate both the adaptive and innate immune responses in lymphocytes. The level of cell-mediated immune responsiveness is determined by measuring the presence or level of an effector molecule produced by immune cells. In a particular embodiment, the whole blood or a fraction thereof comprises T-cells and NK cells. The one or more agents stimulate or potentiate an adaptive immune response via T-cells and innate immunity via NK cells. The assay, therefore, measures the combined adaptive and innate cell-mediated immune potential.

The combined immune response provides a greater measure of cell-mediated immune reactivity compared to adaptive or innate immune reactivity measured singularly. Furthermore, the assay can be conducted using small blood volumes such as from 1 µl to 1000 µl and hence the assay is amenable for finger prick and capillary based sampling. Large volume assays such as from 1.5 ml to 200 ml including 5 ml, 10 ml and 20 ml volumes are also contemplated herein.

The ability to assess combined adaptive and innate immunity is important, for example, to identify disease conditions and therapeutic and environmental agents which induce immunosuppression which could lead to a greater risk of secondary infections.

Accordingly, an aspect of the present invention contemplates a method for measuring cell-mediated immune response activity in a subject, the method comprising contacting a sample source of lymphocytes from the subject with one or more agents which potentiates adaptive and innate immunity and measuring the level of an immune effector molecule produced by immune cells wherein the level of the immune effector molecule is indicative of the level of cell-mediated immunoresponsiveness of the subject.

Another aspect of the present invention provides a method for measuring cell-mediated immune response activity in a subject, the method comprising contacting a sample source of lymphocytes from the subject with one or more agents which potentiate adaptive and innate immunity and measuring the elevation in the level of an immune effector molecule from immune cells wherein the level of the immune effector molecule is indicative of the level of cell-mediated immunoresponsiveness of the subject wherein the level of immunoresponsiveness is indicative of the presence or absence or level or stage of a disease or condition selected from the list comprising an infection by a pathogenic agent, an autoimmune disease, a cancer, an inflammatory condition, exposure to a toxic agent, exposure to a therapeutic agent and an immunodeficiency.

Still another aspect of the present invention contemplates an assay to detect the presence, absence, level or stage of a disease or condition in a subject, the method comprising contacting a sample source of lymphocytes from the subject with one or more agents which potentiate adaptive and innate immunity and measuring the elevation in the level of an immune effector molecule from immune cells wherein the level of the immune effector molecule is indicative of the disease or condition.

Even yet another aspect of the present invention provides a method for monitoring a response to a therapeutic protocol for a disease or condition in a subject, the method comprising contacting a source of lymphocytes from the subject with an agent used in the therapeutic protocol and measuring the presence or elevation in the level of an immune effector molecule from immune cells in the presence of one or more molecules which potentiate adaptive and innate immunity wherein the level of the immune effector molecule is indicative of the efficacy of the therapeutic protocol.

The present invention further contemplates a method for determining whether an agent induces immunosuppression in a subject, the method comprising contacting a source of lymphocytes from the subject after exposure to the agent with one or more potentiators which stimulate adaptive and innate immunity and measuring the presence and level of an effector molecule from the lymphocytes wherein the level of the effector molecule determines the level of immunosuppression induced by the agent.

In an embodiment, the blood sample is co-stimulated with a TLR agonist and a TLR agonist.

In accordance with this aspect, the agent may be a medicament or an environmental toxicant.

The method of the present invention may also be referred to as an "assay". The assay herein is useful inter alia in assessing the general immune responsiveness of a subject or for detecting the immunoresponsiveness to specific disease conditions such as autoimmune disease, Celiac's disease, cancer, infection by a pathogenic organism or agent, exposure to a toxic agent or medicament and immunodeficiency or immunosuppression conditions such as induced by a disease condition. The source of lymphocytes is conveniently whole blood but the present invention contemplates the use of any source of lymphocytes including fractionated samples comprising lymphocytes as well as samples having undergone cell isolation and/or depletion. Micro-samples of blood such as derived from pin pricks and capillary methods also form part of the present invention. The samples comprise at least T-cells (T-lymphocytes) and NK cells (NK-lymphocytes). Reference to "immune cells" includes T-cells.

Optionally, a simple sugar such as dextrose or glucose is added to the reaction mixture. Reference to "whole blood" includes whole blood without dilution as well as whole blood used in an assay at a volume of from about 10% to about 100% of the total sample assay volume (i.e. reaction mixture), including from about 50% to about 100% and 80% to about 100%. Assay volumes may range from 1 µl to greater than 1000 µl including from 1.5 ml to 200 ml such as 5 ml to 20 ml.

One type of agent may be used to potentiate adaptive and innate immunity or two or more types of agents may be employed together. An example includes co-stimulation with a TCR agonist and a TLR agonist. The lymphocytes may also be exposed to a particular antigen to measure the combined antigen-induced adaptive and innate immune response capability of a subject.

The subjects may be human or non-human animals. Hence, the present invention has human medical, veterinary and livestock applications. Humans represent a particularly useful subject in the practice of the present invention.

In another embodiment, the present invention contemplates a method for detecting whether a disease condition is inducing immunosuppression in a subject the method comprising contacting a source of lymphocytes from the subject with a disease condition with one or more agents which potentiate adaptive and innate immunity and measuring the presence or level of an immune effector molecule from the lymphocytes wherein the level of the immune effector molecule is indicative of the extent of immunosuppression induced or associated with the disease condition.

Kits and skin tests also form part of the present invention.

In an embodiment, the sample is whole blood which is collected in collection tubes containing the agents or to which the agents are added for incubation. Generally, blood is maintained in the presence of heparin. Heparin may be in the tube when blood is added or is subsequently added. The use of blood collection tubes is compatible with standard automated laboratory systems and these are amenable to analysis in large-scale and random access sampling. Blood collection tubes also minimize handling costs and reduce laboratory exposure to whole blood and plasma and, hence, reduce the risk of laboratory personnel from contracting a pathogenic agent such as human immunodeficiency virus (HIV), hepatitis B virus (HBV) or hepatitis C virus (HCV). Furthermore, use of the collection tubes to conduct the incubation renders the assay more sensitive than the previously used 24 well culture well plates.

The present invention therefore provides an enhanced cell-mediated immune assay comprising in one embodiment the use of a collection tube, optionally a simple sugar such as dextrose and the incubation step with one or more agents which potentiate adaptive and innate immunity. The incubation step is generally from about 5 to about 50 hours such as 24 hours. An antigen may optionally also be added.

The immune effector molecules are generally a cytokine such as but not limited to IFN-γ, an interleukin (e.g. IL-2, IL-4, IL-6, IL-10, IL-12 or IL-13), Transforming Growth Factor beta (TGFβ) or a Granulocyte or Granulocyte Macrophage Colony Stimulating Factor (G-CSF and GM-CSF, respectively). Other effector molecules are listed in Table 6. The presence or level of the immune effector molecule may be determined at the level of the molecule itself or to the extent to which a gene is expressed encoding the molecule.

The assay of the present invention may also be used in a personalized medicine approach in the management of therapeutic protocols and/or as part of a pathology architecture platform. Such a platform may be web-based or non-web-based. A business method is therefore also provided whereby blood is collected in transportable tubes which is then analyzed for cell-mediated immunoresponsiveness at a defined location and the results then sent in the form of an electronic report via appropriate architecture to a clinical care provider.

In addition, the ability to enable the assay to be conducted in small blood volumes is useful for the pediatric, elderly and infirmed populations.

BRIEF DESCRIPTION OF THE FIGURES

Some figures contain color representations or entities. Color photographs are available from the Patentee upon request or from an appropriate Patent Office. A fee may be imposed if obtained from a Patent Office.

DETAILED DESCRIPTION

Figure 1A:
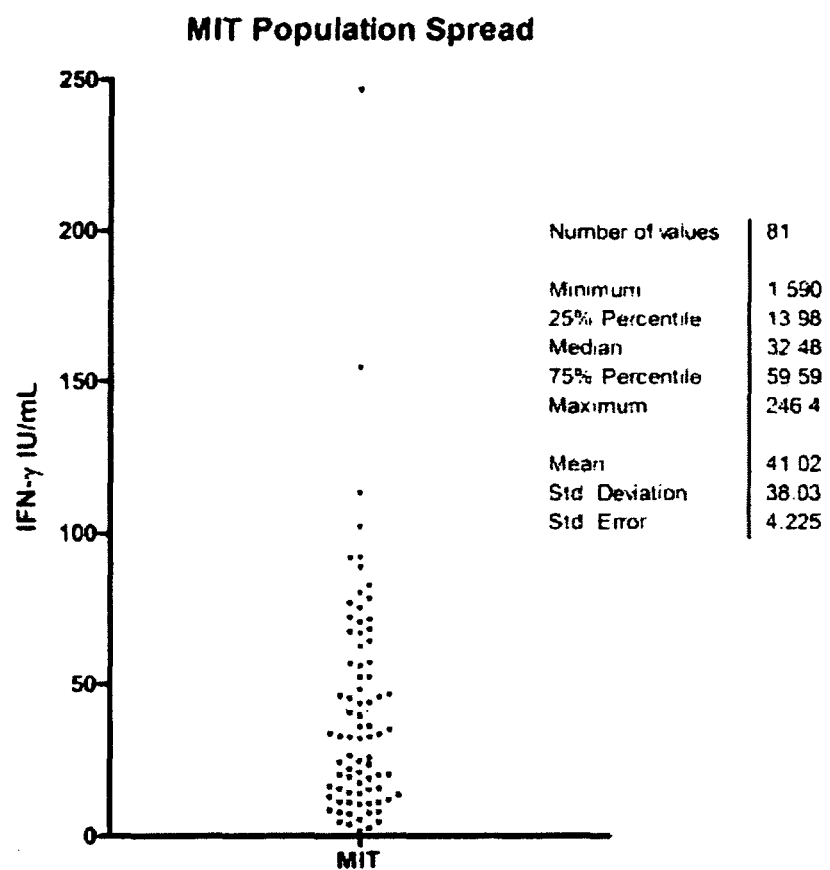
FIGS. 1A through C are graphical representations showing single stimulant IFN-γ responses from whole blood cultures. Normal healthy donor population spread using TCR stimulants mitogen (A) and anti-CD3 antibody (B) or TLR stimulant R848 (C).

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used in the subject specification, the singular forms "a", "an" and "the" include plural aspects unless the context clearly dictates otherwise. Thus, for example, reference to "a T-cell" includes a single T-cell, as well as two or more T-cells; reference to "an agent" includes a single agent, as well as two or more agents; reference to "the invention"

includes single or multiple aspects of an invention; and so forth. The terms "T-cells" and "T-lymphocytes" are used interchangeably herein. An "immune cell" includes a T-cell and cells of the innate immune system such as NK cells.

Reference to an "agent", "reagent", "molecule" and "compound" includes single entities and combinations of two or more of such entities. A "combination" also includes multi-part such as a two-part composition where the agents are provided separately and used or dispensed separately or admixed together prior to dispensation. For example, a multi-part assay pack may have two or more agents which potentiate adaptive and innate immunity separately maintained. In an embodiment, the two agents are a TCR agonist and a TLR agonist. Hence, this aspect of the present invention includes agents dried and loose or immobilized to a compartment wall or solid support in an assay pack. A "combination" also includes a fusion or chimeric molecule comprising an adaptive immunity stimulant and an innate immunity stimulant. The adaptive immunity stimulant may modulate adaptive immunity via T-cell receptor-dependent or -independent means. An example of a TCR agonist is anti-CD3 antibody. A TLR agonist includes a TLR-7/8 agonist such as R848 (imidazoquinoline).

The present invention is predicated in part by the augmentation of production of effector molecules from lymphocytes exposed to adaptive and innate immunity potentiation. This enables a more sensitive assay to assess the cell-mediated immune responsiveness of a subject. The present invention provides, therefore, an assay to detect, assess or otherwise monitor a cell-mediated response in a subject by measuring the presence or level of effector molecules from T-cells stimulated by an adaptive and innate immunity potentiator. Lymphocytes are contacted with an agent which potentiates adaptive and innate immunity Generally, at least two agents are employed wherein at least one potentiates adaptive immunity (via T-cells) and at least one potentiates innate immunity (e.g. via NK cells). In an alternative, a chimeric molecule is used comprising an adaptive immunity stimulant and an innate immunity stimulant. The adaptive immunity stimulant may be via T-cell receptor dependent or independent means. The present invention provides, therefore, a means to determine the responsiveness of cell-mediated immunity in a subject and, in turn, provides a means for determining whether a disease condition or an agent induces or is associated with immunosuppression. The method also enables diagnosis of infectious diseases, pathological conditions, determination of the level of immunocompetence and assessing of adaptive and innate immune cell responsiveness to endogenous or exogenous agents as well as assessing exposure to a toxic agent such as beryllium or other toxicants.

Accordingly, aspect of the present invention contemplates a method for measuring cell-mediated immune response activity in a subject, the method comprising contacting a source of lymphocytes from the subject with one or more agents which potentiates adaptive and innate immunity and measuring the level of an immune effector molecule produced by immune cells wherein the level of the immune effector molecule is indicative of the level of cell-mediated immunoresponsiveness of the subject.

Another aspect of the present invention contemplates a method for measuring cell-mediated immune response activity in a subject, the method comprising contacting a source of lymphocytes from the subject with one or more agents which potentiate adaptive and innate immunity and measuring the elevation in the level of an immune effector molecule from immune cells wherein the level of the immune effector molecule is indicative of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to a toxic agent.

Yet another aspect of the present invention provides a method for measuring cell-mediated immune response activity in a subject, the method comprising contacting a source of lymphocytes from the subject with one or more agents which potentiate adaptive and innate immunity and measuring the elevation in the level of an immune effector molecule from immune cells wherein the level of the immune effector molecule is indicative of the level of cell-mediated responsiveness and is indicative of the presence or absence or level or stage of a disease or condition selected from the list comprising an infection by a pathogenic agent, an autoimmune disease, a cancer, an inflammatory condition and exposure to a toxic agent.

Still another aspect of the present invention contemplates an assay to detect the presence, absence, level or stage of a disease or condition in a subject, the method comprising contacting a source of lymphocytes from the subject with one or more agents which potentiate adaptive and innate immunity and measuring the elevation in the level of an immune effector molecule from immune cells wherein the level of the immune effector molecule is indicative of the disease or condition.

The present invention further contemplates a method for determining whether an agent induces immunosuppression in a subject, the method comprising contacting a source of lymphocytes from the subject after exposure to the agent with one or more potentiators which stimulate adaptive and innate immunity and measuring the presence and level of an effector molecule from the lymphocytes wherein the level of the effector molecule determines the level of immunosuppression induced by the agent.

In accordance with this aspect, the agent may be a medicament or an environmental toxicant.

In an embodiment, the blood sample is co-stimulated with a TCR agonist (e.g. anti-CD3 antibody) and a TLR agonist (e.g. TLR-7/8 agonist, imidazoquinoline [R848]).

Hence, the present invention contemplates a method for measuring cell-mediated immune response activity in a subject, the method comprising contacting a source of lymphocytes from the subject with a TCR agonist and a TLR agonist to potentiate the adaptive and innate immunity and measuring the level of an immune effector molecule produced by immune cells wherein the level of the immune effector molecule is indicative of the level of cell-mediated immunoresponsiveness of the subject.

Another aspect of the present invention contemplates a method for measuring cell-mediated immune response activity in a subject, the method comprising contacting a source of lymphocytes from the subject with a TCR agonist and a TLR agonist which potentiate adaptive and innate immunity and measuring the elevation in the level of an immune effector molecule from immune cells wherein the level of the immune effector molecule is indicative of the level of cell-mediated responsiveness of the subject wherein the level of responsiveness is indicative of the presence or absence or level or stage of a disease or condition selected from the list comprising an infection by a pathogenic agent, an autoimmune disease, a cancer, an inflammatory condition and exposure to a toxic agent.

A use is also provided for a TCR agonist and a TLR agonist which potentiate adaptive and innate immunity in the manufacture of a diagnostic assay of cell-mediated immune responsiveness by the method of incubating lymphocytes with one or more molecules which potentiate the adaptive and innate immune system and detecting the presence or elevation in an effector molecule.

In another embodiment, the present invention contemplates a method for detecting whether a disease condition is inducing immunosuppression in a subject the method comprising contacting a source of lymphocytes from the subject with a disease condition with one or more agents which potentiate adaptive and innate immunity and measuring the presence or level of an immune effector molecule from the lymphocytes wherein the level of the immune effector molecule is indicative of the extent of immunosuppression induced or associated with the disease condition.

A use is also provided for one or more agents which potentiate adaptive and innate immunity in the manufacture of a diagnostic assay of cell-mediated immune responsiveness by the method of incubating lymphocytes with one or more molecules which potentiate the adaptive and innate immune system and detecting the presence or elevation in an effector molecule.

This use includes the use for detecting or monitoring the presence, absence, level or stage of a disease or condition such as an infection by a pathogenic agent, an autoimmune disease, a cancer, an inflammatory condition and/or exposure to a medicament or a toxic agent such as a beryllium or other environmental toxicant. Measuring "an immune effector molecule" includes measuring one or more different types of molecules.

Reference to the potentiation of adaptive and innate immunity includes stimulating T-cell receptor-dependent and/or -independent immunity and Toll-like receptor (TLR)-dependent immunity such as mediated by NK cells. By "immune cells" is meant to include "T-cells". An additional agent may also be added to modulate regulatory T-cell (T-reg cells) activity. The latter encompasses inhibiting the suppressor function of T-reg cells. Agents which modulate T-reg cells encompassed herein include a CD25 ligand; a sense or antisense oligonucleotide to genetic material encoding JAK1 or TYK2; a neutralizing antibody; a CpG containing oligonucleotide; an oligonucleotide acting as a TLR modulating agent; and other TLR modulating agents.

In a particular embodiment, the T-reg cells are immune response suppressor cells the activity of which is inhibited.

Accordingly, the present invention is further directed to a method for measuring cell-mediated immune response activity in a subject, the method comprising contacting a source of regulatory T-cells from the subject with an agent selected from (i) an inhibitor of suppressor regulatory T-cells; and (ii) an activator of immune augmenting cells or a subset thereof; and further contacting T-cells with one or more agents which potentiate adaptive and innate immunity and measuring the elevation in the level of an immune effector molecule from immune cells wherein the level of the immune effector molecule is indicative of the level of cell-mediated responsiveness of the subject.

Examples of inhibitors or modulators of T-reg function include CD25 ligands such as but not limited to a polyclonal or monoclonal antibody to CD25 or an antigen-binding fragment thereof, humanized or deimmunized polyclonal or monoclonal antibodies to CD25 or a recombinant or synthetic form of the polyclonal or monoclonal antibodies.

Other examples of agents include sense or antisense nucleic and molecules directed to the mRNA or DNA (i.e. genetic material) encoding Janus Tyrosine Kinase 1 (JAK1) or Tyrosine Kinase 2 (TYK2) or small molecule inhibitors of JAK1 or TYK2 proteins. Reference to "small molecules" includes immunoglobulin new antigen receptors (IgNARs) as described in International Patent Publication No. WO 2005/118629. Yet still further examples of suitable agents stimulating agents such as CpG molecules which act via Toll-like receptors (TLRs) and/or other mechanisms. Hence, CpG containing oligonucleotides and an oligonucleotide acting as a TLR modulating agent also form part of the present invention.

A single type of agent may be used or two or more types of agents may be employed to modulate T-reg cells. For example, the assay may be conducted with a CD25 ligand and a JAK1/TYK2 sense or antisense oligonucleotide; a CD25 ligand and a TLR modulating agent; a JAK1/TYK2 sense or antisense oligonucleotide and a TLR modulating agent; or a CD25 ligand, a JAK1/TYK2 sense or antisense oligonucleotide and a TLR modulating agent. Alternatively, just one type of agent is employed. In another alternative, a CpG comprising oligonucleotide and a TLR modulating agent is used.

In accordance with the various aspects of the present invention, the lymphocyte/immune cells may also be exposed to an antigen to measure antigen-induced adaptive and innate immunoresponsiveness.

Reference to a "subject" includes a human or non-human species including primates, livestock animals (e.g. sheep, cows, pigs, horses, donkey, goats), laboratory test animals (e.g. mice, rats, rabbits, guinea pigs, hamsters), companion animals (e.g. dogs, cats), avian species (e.g. poultry birds, aviary birds), reptiles and amphibians. The present invention has applicability, therefore, in human medicine as well as having livestock and veterinary and wild-life applications which includes the horse, dog and camel racing industries. For example, the assay of the present invention may be routinely carried out on horses before and/or after heavy exertion (such as a race) to screen for evidence of exercise-induced pulmonary hemorrhage (EIPH). All horses exhibit some form of EIPH to some degree during exercise. However, sub-clinical forms of EIPH can be hard to detect.

Reference to a human includes particular populations of humans such as pediatric, elderly and infirmed populations as well as particular cohorts or populations of a particular ethnicity.

In another embodiment, the subject is a human and the cell-mediated immune response assay is used in screening for responsiveness to pathogenic microorganisms, viruses and parasites, potential for development or monitoring auto-immune conditions, Celiac's disease, monitoring a subject's response to oncological challenge and for determining the presence of any immunodeficiency or immunosuppression. The latter may occur, for example, due to certain medicaments including various chemotherapeutic agents. Alternatively, exposure to environmental toxicants and pollutants.

The immune effector molecules may be any of a range of molecules which are produced in response to cell activation or stimulation by an antigen. Although an interferon (IFN) such as IFN-γ is a particularly useful immune effector molecule, others include a range of cytokines such as interleukins (IL), e.g. IL-2, IL-4, IL-6, IL-10, IL-12 or IL-13, Tumor Necrosis Factor alpha (TNF-α), Transforming Growth Factor beta (TGF-β), a Colony Stimulating Factor (CSF) such as Granulocyte (G)-CSF or Granulocyte Macrophage (GM)-CSF amongst many others such as complement or components in the complement pathway. Other effector molecules which may be profiled include those listed in Table 6.

Examples of T-cell receptor agonists include PHA, staphylococcal enterotoxin B (SEB), CpG oligonucleotides, antibodies to the T-cell receptor complex and anti-CD3 antibodies. Examples of T-cell receptor-independent adaptive immune stimulants include PMA and ConA. TLR agonists include Pam3CSK4 (TLR-2 ligand), Lipomannan (TLR-2 ligand), poly(I:C)— (TLR-3 ligand), Lipopolysaccharide (TLR-4 ligand), an imidazoquinoline compound such as R848 (TLR-7/8 ligand) and CpG oligodeoxynucleotides (TLR-9 ligand). In terms of selecting a TLR agonist, in decreasing order, agonists are selected from agonists for TLR-7/8>TLR-4>TLR-3>TLR-2.

A "CpG molecule" means an oligonucleotide comprising a CpG sequence or motif. The present invention extends to any modulator of Toll-like receptor (TLR) function or other aspect of the immune system.

The present invention also provides a method for measuring cell-mediated immune response activity in a subject, the method comprising contacting a source of lymphocytes from the subject with a TLR agonist and an adaptive immunity stimulant and measuring the level of an immune effector molecule from immune cells wherein the level of the immune effector molecule is indicative of the level of cell-mediated responsiveness of the subject.

The assay of the present invention enables detection of the presence or absence or level or stage of a disease or condition in a subject such as infection by a pathogenic agent, an autoimmune disease, cancer, exposure to an inflammatory agent exposure to a medicament, exposure to a toxic agent such as beryllium or other toxicant or pollutant and immunodeficiency or immunosuppression such as induced by a disease condition.

The adaptive and innate immunity agent(s) may be free standing in a reactive vessel or may be immobilized to a solid support such as a bead or a side or bottom of a reaction vessel. The agent(s) may also be in dried form which is re-constituted prior to or during use. Similarly, if an antigen is included, the antigen may be free standing or immobilized in a reactive vessel such as to the vessel itself or a bead or other solid support.

In one embodiment, the sample collected from the subject is generally deposited into a blood collection tube. A blood collection tube includes a blood draw tube or other similar vessel. Conveniently, when the sample is whole blood, the blood collection tube is heparinized. Alternatively, heparin is added to the tube after the blood is collected. Notwithstanding that whole blood is particularly contemplated and a most convenient sample, the present invention extends to other samples containing immune cells such as lymph fluid, cerebral fluid, tissue fluid and respiratory fluid including nasal and pulmonary fluid as well as samples having undergone cell depletion. Reference to "whole blood" includes whole blood which has not been diluted such as with tissue culture, medium, reagents, excipients, etc. In one embodiment, the term "whole blood" includes an assay sample (i.e. reaction mixture) comprising at least 10% by volume whole blood. The term "at least 10% by volume" includes blood volumes of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100% by volume of total assay volume of the reaction mixture.

Additional agents may be added such as culture media, enzymes, excipients antigen and the like without departing from the sample comprising "whole blood".

Small blood volumes may also be used such as for 1 µl to 1000 µl. Examples include 5 µl, 10 µl, 20 µl, 50 µl, 100 µl and 500 µl as well as fractions in between. Hence, sample volumes include from about 1 µl to about 200 ml including 1 ml, 5 ml, 10 ml and 20 ml.

The use of blood collection tubes is compatible with standard automated laboratory systems and these are amenable to analysis in large-scale and random access sampling. Blood collection tubes also minimize handling costs and reduce laboratory exposure to whole blood and plasma and, hence, reduce the risk of laboratory personnel from contracting a pathogenic agent such as HIV or hepatitis B virus (HBV) or hepatitis C virus (HCV).

Combining the incubation step with the collection tube is particularly efficacious and enhances the sensitivity of the assay as does the optional feature of incubating the cells in the presence of a simple sugar such as dextrose or glucose.

The cells of the cell-mediated immune system lose the capacity to mount an immune response in whole blood after extended periods following blood draw from the subject, and responses without intervention are often severely reduced or absent 24 hours following blood draw. The reduction of labor and need for specialized plastic ware allows cell-mediated immune stimulation with antigens to be performed at the point of care locations such as physicians' offices, clinics, outpatient facilities and veterinary clinics or on farms. Once antigen stimulation is complete, the requirement for fresh and active cells no longer exists. IFN-γ and other cytokines or immune effector molecules are stable in plasma and, thus, the sample can be stored, or shipped without special conditions or rapid time requirements.

The incubation step may be from 1 to 50 hours, such as 1 to 40 hours or 8 to 24 hours or a time period in between including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 hours. A period of 24 hours is particularly convenient.

The ability to measure cell-mediated immunity is important for assessing a subject's ability to respond to an infection by a pathogenic agent such as a microorganism or virus or parasite, to mount an autoimmune response such as in autoimmune diabetes or to protect against cancers or other oncological conditions or to detect an inflammatory condition or to detect exposure or sensitivity of a subject to a toxic agent such as beryllium. The assay described herein also enables detection of disease conditions which lead to immunosuppression or immunosuppresion induced by medicaments Consequently, reference to "measuring a cell-mediated immune response in a subject" includes and encompasses immune diagnosis of infectious and autoimmune diseases, a marker for immunocompetence as well as a marker for inflammatory diseases, cancer and toxic agents. Importantly, the combined adaptive and innate immune responsiveness is determined. Furthermore, the ability to use small blood volumes enables assays to be readily conducted on, for example, the pediatric, elderly and infirmed populations.

In an embodiment, disease conditions leading to immunosuppression include chronic infection and cancer. Medicaments which can lead to immunosuppression include those used to treat rheumatoid arthritis, cancer and inflammatory bowel disease. Pathogenic or infectious agents include bacteria, parasites and viruses. Examples of bacteria include Gram positive and Gram negative microorganisms such as *Mycobacterium* species, *Staphylococcus* species, *Streptococcus* species, *Escherichia coli*, *Salmonella* species, *Clostridium* species, *Shigella* species, *Proteus* species, *Bacillus* species, *Hemophilus* species, *Borrelia* species amongst others. *Mycobacterium tuberculosis* is a particularly useful target as well as conditions arising from infection by *M. tuberculosis* such as tuberculosis (TB). Examples of viruses include Hepatitis virus (Hepatitis B virus and Hepatitis C virus), Herpes virus and Human immune deficiency virus (HIV) as well as diseases resulting therefrom. Parasites include *Plasmodium* species, ringworm, liver parasites and the like. Other pathogenic agents include eukaryotic cells such as yeasts and fungi.

Autoimmune diseases contemplated herein for detection include inter alia alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid, cardiomyopathy, celiac sprue-dermatitis, chronic fatigue syndrome (CFIDS), chronic inflammatory demyelinating, chronic inflammatory polyneuropathy, Churg-Strauss syndrome, cicatricial pemphigoid, crest syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arrthritis, sarcoidosis, scleroderma, Sjogren's syndrome, stiff-man syndrome, systemic lupus erythematosus, Takayasu arteritis, temporal arteritis/ giant cell arteritis, ulcerative colitis, uveitis, vasculitis and vitiligo.

It is generally important to assess the potential or actual cell-mediated responsiveness in subjects exposed to these infectious entities. The method of the present invention can also be used to detect the presence or absence of these conditions as well as the level or stage of disease process.

Other disease conditions which can lead to immunosuppression include inflammatory disease conditions.

Examples of inflammatory disease conditions contemplated by the present invention include but are not limited to those disease and disorders which result in a response of redness, swelling, pain, and a feeling of heat in certain areas that is meant to protect tissues affected by injury or disease. Inflammatory diseases which can be treated using the methods of the present invention, include, without being limited to, acne, angina, arthritis, aspiration pneumonia, disease, empyema, gastroenteritis, inflammation, intestinal flu, NEC, necrotizing enterocolitis, pelvic inflammatory disease, pharyngitis, PID, pleurisy, raw throat, redness, rubor, sore throat, stomach flu and urinary tract infections, chronic inflammatory demyelinating polyneuropathy, chronic inflammatory demyelinating polyradiculoneuropathy, chronic inflammatory demyelinating polyneuropathy, chronic inflammatory demyelinating polyradiculoneuropathy. In terms of non-human applications, the present invention extends to detecting EIPH in horses and various conditions in animals such as facial tumor disease in the Tasmanian Devil.

Cancer therapy also is somewhat dependent on cell-mediated immunity and the cancer itself or drugs used to treat cancer can lead to immunosuppression. Cancers contemplated herein include: a group of diseases and disorders that are characterized by uncontrolled cellular growth (e.g. formation of tumor) without any differentiation of those cells into specialized and different cells. Such diseases and disorders include ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/–ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor.

As indicated above, the lymphocyte immune cells may also be exposed to an antigen to measure antigen-induced combined adaptive and innate immunity.

The detection of the immune effector molecules may be measured at the protein or nucleic acid levels. Consequently, reference to "presence or level" of the immune effector molecule includes direct and indirect data. For example, high levels of cytokine mRNA are indirect data showing increased levels of the cytokine.

Ligands to the immune effectors are particularly useful in detecting and/or quantitating these molecules. Antibodies to the immune effectors are particularly useful. Techniques for the assays contemplated herein are known in the art and include, for example, radioimmunoassay, sandwich assays, ELISA and ELISpot. Reference to "antibodies" includes parts of antibodies, mammalianized (e.g. humanized) antibodies, deimmunized antibodies, recombinant or synthetic antibodies and hybrid and single chain antibodies. For skin tests, in humans, humanized or deimmunized antibodies are particularly contemplated herein to detect effector molecules.

Both polyclonal and monoclonal antibodies are obtainable by immunization with the immune effector molecules or antigenic fragments thereof and either type is utilizable for immunoassays. Methods of obtaining both types of sera are well known in the art. Polyclonal sera are less preferred but are relatively easily prepared by injection of a suitable laboratory animal with an effective amount of the immune effector, or antigenic part thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly useful because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates, therefore, a method for detecting an immune effector molecule in a sample comprising lymphocytes from a subject, the method comprising contacting the sample or an aliquot of the sample with an antibody specific for the immune effector molecule or an antigenic fragment thereof for a time and under conditions sufficient for an antibody-effector complex to form, and then detecting the complex wherein the immune effector molecule is generated after incubation of the lymphocytes with one or more agents which potentiate the adaptive and innate immune systems.

A "sample" includes whole blood or a fraction thereof comprising lymphocytes. This method includes micro-arrays, macro-arrays and nano-arrays on planar or spherical solid supports. A micro- or macro-array is useful. A "sample" also includes a small volume sample of from about 1 μl to 1000 μl including 5 μl, 20 μl, 50 μl and 100 μl.

A wide range of immunoassay techniques are available as can be seen by reference to U.S. Pat. Nos. 4,016,043, 4,424,279 and 4,018,653.

The following is a description of one type of assay. An unlabeled antibody is immobilized on a solid substrate and the sample to be tested for the immune effector molecules (e.g. cytokines) brought into contact with the bound molecule. After a suitable period of incubation, for a period of time sufficient to allow formation of an antibody-immune effector molecule complex, a second antibody specific to the effector molecule, labeled with a reporter molecule capable of producing a detectable signal, is then added and incubated, allowing time sufficient for the formation of another complex of antibody-effector-labeled antibody. Any unreacted material is washed away, and the presence of the effector molecule is determined by observation of a signal produced by the reporter molecule. The results may either be qualitative, by simple observation of the visible signal, or may be quantitated by comparing with a control sample containing known amounts of antigen. This generalized technique is well known to those skilled in the art as would be any of a number of variations.

In these assays, a first antibody having specificity for the instant immune effectors is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, spheres, discs of microplates, or any other surface suitable for conducting an immunoassay. The binding processes are well known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-120 minutes or where more convenient, overnight) and under suitable conditions (e.g. for about 20° C. to about 40° C.) to allow binding of any subunit present in the antibody. Following the incubation period, the antibody subunit solid phase is washed and dried and incubated with a second antibody specific for a portion of the effector molecule. The second antibody is linked to a reporter molecule which is used to indicate the binding of the second antibody to the effector molecule.

There is many variations to this assay. One particularly useful variation is a simultaneous assay where all or many of the components are admixed substantially simultaneously. Furthermore, binding of an antibody to a cytokine may be determined by binding of a labeled antibody directed to the first mentioned antibody.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules. Examples of suitable fluorophores are provided in Table 1. In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. Again, the present invention extends to a substantially simultaneous assay.

Alternately, fluorescent compounds, such as fluorescein and rhodamine, may be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. The fluorescent labeled antibody is allowed to bind to the first antibody-antigen complex. After washing off the unbound reagent, the remaining tertiary complex is then exposed to the light of the appropriate wavelength the fluorescence observed indicates the presence of the antigen of interest. Immunofluorescene and enzyme immunoassay techniques are both very well established in the art and are particularly preferred for the present method. However, other reporter molecules, such as radioisotope, chemiluminescent or bioluminescent molecules, may also be employed.

There are a range of other detection systems which may be employed including colloidal gold and all such detection systems are encompassed by the present invention.

The present invention also contemplates genetic assays such as involving PCR analysis to detect RNA expression products of a genetic sequence encoding an immune effector.

In one embodiment, PCR is conducted using pairs of primers, one or both of which are generally labeled with the same or a different reporter molecule capable of giving a distinguishable signal. The use of fluorophores is particularly useful in the practice of the present invention. Examples of suitable fluorophores may be selected from the list given in Table 1. Other labels include luminescence and phosphorescence as well as infrared dyes. These dyes or fluorophores may also be used as reporter molecules for antibodies.

TABLE 1

List of suitable fluorophores

| Probe | Ex[1] (nm) | Em[2] (nm) |
|---|---|---|
| Reactive and conjugated probes | | |
| Hydroxycoumarin | 325 | 386 |
| Aminocoumarin | 350 | 455 |
| Methoxycoumarin | 360 | 410 |
| Cascade Blue | 375; 400 | 423 |
| Lucifer Yellow | 425 | 528 |
| NBD | 466 | 539 |
| R-Phycoerythrin (PE) | 480; 565 | 578 |
| PE-Cy5 conjugates | 480; 565; 650 | 670 |
| PE-Cy7 conjugates | 480; 565; 743 | 767 |
| APC-Cy7 conjugates | 650; 755 | 767 |
| Red 613 | 480; 565 | 613 |
| Fluorescein | 495 | 519 |
| FluorX | 494 | 520 |
| BODIPY-FL | 503 | 512 |
| TRITC | 547 | 574 |
| X-Rhodamine | 570 | 576 |
| Lissamine Rhodamine B | 570 | 590 |
| PerCP | 490 | 675 |
| Texas Red | 589 | 615 |
| Allophycocyanin (APC) | 650 | 660 |
| TruRed | 490, 675 | 695 |
| Alexa Fluor 350 | 346 | 445 |
| Alexa Fluor 430 | 430 | 545 |
| Alexa Fluor 488 | 494 | 517 |
| Alexa Fluor 532 | 530 | 555 |
| Alexa Fluor 546 | 556 | 573 |
| Alexa Fluor 555 | 556 | 573 |
| Alexa Fluor 568 | 578 | 603 |
| Alexa Fluor 594 | 590 | 617 |
| Alexa Fluor 633 | 621 | 639 |
| Alexa Fluor 647 | 650 | 688 |
| Alexa Fluor 660 | 663 | 690 |
| Alexa Fluor 680 | 679 | 702 |
| Alexa Fluor 700 | 696 | 719 |
| Alexa Fluor 750 | 752 | 779 |
| Cy2 | 489 | 506 |
| Cy3 | (512); 550 | 570; (615) |
| Cy3,5 | 581 | 596; (640) |
| Cy5 | (625); 650 | 670 |
| Cy5,5 | 675 | 694 |
| Cy7 | 743 | 767 |
| Nucleic acid probes | | |
| Hoeschst 33342 | 343 | 483 |
| DAPI | 345 | 455 |
| Hoechst 33258 | 345 | 478 |
| SYTOX Blue | 431 | 480 |
| Chromomycin A3 | 445 | 575 |
| Mithramycin | 445 | 575 |
| YOYO-1 | 491 | 509 |
| SYTOX Green | 504 | 523 |
| SYTOX Orange | 547 | 570 |
| Ethidium Bormide | 493 | 620 |
| 7-AAD | 546 | 647 |
| Acridine Orange | 503 | 530/640 |
| TOTO-1, TO-PRO-1 | 509 | 533 |
| Thiazole Orange | 510 | 530 |
| Propidium Iodide (PI) | 536 | 617 |
| TOTO-3, TO-PRO-3 | 642 | 661 |
| LDS 751 | 543; 590 | 712; 607 |
| Fluorescent Proteins | | |
| Y66F | 360 | 508 |
| Y66H | 360 | 442 |
| EBFP | 380 | 440 |
| Wild-type | 396, 475 | 50, 503 |
| GFPuv | 385 | 508 |
| ECFP | 434 | 477 |
| Y66W | 436 | 485 |
| S65A | 471 | 504 |
| S65C | 479 | 507 |
| S65L | 484 | 510 |
| S65T | 488 | 511 |
| EGFP | 489 | 508 |
| EYFP | 514 | 527 |
| DsRed | 558 | 583 |
| Other probes | | |
| Monochlorobimane | 380 | 461 |
| Calcein | 496 | 517 |

[1]Ex: Peak excitation wavelength (nm)
[2]Em: Peak emission wavelength (nm)

Any suitable method of analyzing fluorescence emission is encompassed by the present invention. In this regard, the present invention contemplates techniques including but not restricted to 2-photon and 3-photon time resolved fluorescence spectroscopy as, for example, disclosed by Lakowicz et al, *Biophys. J.* 72:567, 1997, fluorescence lifetime imaging as, for example, disclosed by Eriksson et al, *Biophys. J.* 2:64, 1993 and fluorescence resonance energy transfer as, for example, disclosed by Youvan et al., *Biotechnology et elia* 3:1-18, 1997.

Luminescence and phosphorescence may result respectively from a suitable luminescent or phosphorescent label as is known in the art. Any optical means of identifying such label may be used in this regard.

Infrared radiation may result from a suitable infrared dye. Exemplary infrared dyes that may be employed in the present invention include but are not limited to those disclosed in Lewis et al, *Dyes Pigm.* 42(2):197, 1999, Tawa et al, *Mater. Res. Soc. Symp. Proc.* 488 [Electrical, Optical and Magnetic Properties of Organic Solid-State Materials IV], 885-890, Daneshvar et al, *J. Immunol. Methods* 226(1-2): 119-128, 1999, Rapaport et al, *Appl. Phys. Lett.* 74(3):329-331, 1999 and Durig et al, *J. Raman Spectrosc.* 24(5):281-285, 1993. Any suitable infrared spectroscopic method may be employed to interrogate the infrared dye. For instance, fourier transform infrared spectroscopy as, for example, described by Rahman et al, *J. Org. Chem.* 63:6196, 1998 may be used in this regard.

Suitably, electromagnetic scattering may result from diffraction, reflection, polarization or refraction of the incident electromagnetic radiation including light and X-rays. Such scattering can be used to quantitate the level of mRNA or level of protein.

Flow cytometry is particularly useful in analyzing fluorophore emission.

As is known in the art, flow cytometry is a high throughput technique which involves rapidly analyzing the physical and chemical characteristics of particles (e.g. labeled mRNA; DNA or proteins) as they pass through the path of one or more laser beams while suspended in a fluid stream. As each particle intercepts the laser beam, the scattered light and fluorescent light emitted by each cell or particle is detected and recorded using any suitable tracking algorithm as, for example, described hereunder.

A modern flow cytometer is able to perform these tasks up to 100,000 cells/particles $s^{-1}$. Through the use of an optical array of filters and dichroic mirrors, different wavelengths of fluorescent light can be separated and simultaneously detected. In addition, a number of lasers with different excitation wavelengths may be used. Hence, a variety of fluorophores can be used to target and examine, for example, different immune effectors within a sample or immune effectors from multiple subjects.

Suitable flow cytometers which may be used in the methods of the present invention include those which measure five to nine optical parameters (see Table 2) using a single excitation laser, commonly an argon ion air-cooled laser operating at 15 mW on its 488 nm spectral line. More advanced flow cytometers are capable of using multiple excitation lasers such as a HeNe laser (633 nm) or a HeCd laser (325 nm) in addition to the argon ion laser (488 or 514 nm).

TABLE 2

Exemplary optical parameters which may be measured by a flow cytometer.

| Parameter | Acronym | Detection angle form incident laser beam | Wavelength (nm) |
| --- | --- | --- | --- |
| Forward scattered light | FS | 2-5° | 488* |
| Side scattered light | SS | 90° | 488* |
| "Green" fluorescence | FL1 | 90° | 510-540† |
| "Yellow" fluorescence | FL2 | 90° | 560-580† |
| "Red" fluorescence | FL3 | 90° | >650# |

*using a 488 nm excitation laser
†width of bandpass filter
longpass filter

For example, Biggs et al, *Cytometry* 36:36-45, 1999 have constructed an 11-parameter flow cytometer using three excitation lasers and have demonstrated the use of nine distinguishable fluorophores in addition to forward and side scatter measurements for purposes of immunophenotyping (i.e. classifying) particles. Selection of parameters can be adequately used depends heavily on the extinction coefficients, quantum yields and amount of spectral overlap between all fluorophores (Malemed et al, "*Flow cytometry and sorting*", $2^{nd}$ Ed., New York, Wiley-Liss, 1990). It will be understood that the present invention is not restricted to any particular flow cytometer or any particular set of parameters. In this regard, the invention also contemplates use in place of a conventional flow cytometer, a microfabricated flow cytometer as, for example, disclosed by Fu et al, *Nature Biotechnology* 17:1109-1111, 1999.

The assay of the present invention may be automated or semi-automated for high throughput screening or for screening for a number of immune effectors from the one subject. The automation is conveniently controlled by computer software.

The present invention further contemplates therefore web-based and non-web-based systems where data on the cell-mediated immunoresponsiveness of a subject are provided by a client server or other architecture platform to a central processor which analyses and compares to a control and optionally considers other information such as patient age, sex, weight and other medical conditions and then provides a report, such as, for example, a risk factor for disease severity or progression or status or an index of probability of disease development. A business method is therefore also provided whereby blood is collected in transportable tubes which is then analyzed for cell-mediated immunoresponsiveness at a defined location and the results then sent in the form of an electronic report via a client server or other architecture platform to a clinical care provider.

Hence, knowledge-based computer software and hardware also form part of the present invention. This facilitate clinical care to ascertain whether a disease condition including infection, cancer of inflammation or a medicament or toxicant is inducing or is associated with immunosuppression.

In particular, the assays of the present invention may be used in existing or newly developed knowledge-based architecture or platforms associated with pathology services. For example, results from the assays are transmitted via a communications network (e.g. the internet) or telephone connection to a processing system in which an algorithm is stored and used to generate a predicted posterior probability value which translates to the index of cell-mediated immunoresponsiveness or immunosuppression which is then forwarded to an end user in the form of a diagnostic or predictive report. This report may also form the basis of clinical care management and personalized medicine.

The assay may, therefore, be in the form of a kit or computer-based system which comprises the reagents necessary to detect the concentration of the immune effector molecule following exposure of lymphocytes to one or more agents which potentiate adaptive and innate immunity and the computer hardware and/or software to facilitate determination and transmission of reports to a clinician.

For example, the present invention contemplates a method of allowing a user to determine the status of cell-mediated immunoresponsiveness of a subject, the method including:

(a) receiving data in the form of levels or concentrations of an immune effector molecule which relative to a control provide a correlation to the state of cell-mediated immunoresponsiveness from the user via a communications network, the immune effector molecule measured after exposure of lymphocytes to one or more agents which potentiate adaptive and innate immune responses;

(b) processing the subject data via univariate or multivariate analysis to provide an immunoresponsiveness value;

(c) determining the status of the subject in accordance with the results of the immunoresponsiveness value in comparison with predetermined values; and (d) transferring an indication of the status of the subject to the user via the communications network.

Reference to the "univariate" or "multivariate" analysis includes an algorithm which performs the univariate or multivariate analysis function.

Conveniently, the method generally further includes:

(a) having the user determine the data using a remote end station; and (b) transferring the data from the end station to the base station via the communications network.

The base station can include first and second processing systems, in which case the method can include:

(a) transferring the data to the first processing system;

(b) transferring the data to the second processing system; and (c) causing the first processing system to perform the univariate or multivariate analysis function to generate the cell-mediated immunoresponsiveness value.

The method may also include:

(a) transferring the results of the univariate or multivariate analysis function to the first processing system; and (b) causing the first processing system to determine the status of the subject.

In this case, the method also includes at least one of: (a) transferring the data between the communications network and the first processing system through a first firewall; and (b) transferring the data between the first and the second processing systems through a second firewall.

The second processing system may be coupled to a database adapted to store predetermined data and/or the univariate or multivariate analysis function, the method including:

(a) querying the database to obtain at least selected predetermined data or access to the univariate or multivariate analysis function from the database; and (b) comparing the selected predetermined data to the subject data or generating a predicted probability index of a level of cellular immunoresponsiveness or immunosuppression.

The second processing system can be coupled to a database, the method including storing the data in the database.

The method can also include having the user determine the data using a secure array, the secure array of elements capable of determining the level of immune effector molecule and having a number of features each located at respective position(s) on the respective code. In this case, the method typically includes causing the base station to:

(a) determine the code from the data;

(b) determine a layout indicating the position of each feature on the array; and (c) determine the parameter values in accordance with the determined layout, and the data.

The method can also include causing the base station to:

(a) determine payment information, the payment information representing the provision of payment by the user; and (b) perform the comparison in response to the determination of the payment information.

The present invention also provides a base station for determining the status of a subject with respect to cell-mediated immunoresponsiveness or immunosuppression, the base station including:

(a) a store method;

(b) a processing system, the processing system being adapted to:

(c) receive subject data from the user via a communications network, the data including levels of immune effector molecule wherein the level of the effector molecule relative to a control provides a correlation to the state of cell-mediated immunoresponsiveness wherein the immune effector molecule is determined after exposure of lymphocytes to one, or more agents which potentiate the adaptive and innate immune system;

(d) performing an algorithmic function including comparing the data to predetermined data;

(e) determining the status of the subject in accordance with the results of the algorithmic function including the comparison; and (c) output an indication of the status of the subject to the user via the communications network.

The processing system can be adapted to receive data from a remote end station adapted to determine the data.

The processing system may include:

(a) a first processing system adapted to:

(i) receive the data; and (ii) determine the status of the subject in accordance with the results of the univariate or multivariate analysis function including comparing the data; and (b) a second processing system adapted to:

(i) receive the data from the processing system;

(ii) perform the univariate or multivariate analysis function including the comparison; and (iii) transfer the results to the first processing system.

The base station typically includes:

(a) a first firewall for coupling the first processing system to the communications network; and (b) a second firewall for coupling the first and the second processing systems.

The processing system can be coupled to a database, the processing system being adapted to store the data in the database.

In accordance with this embodiment, levels of the immune effector molecule may be screened alone or in combination with other biomarkers or disease indicators. An "altered" level means an increase or elevation or a decrease or reduction in the concentrations of the immune effector molecule.

The determination of the concentrations or levels of the immune effector molecule enables establishment of a diagnostic rule based on the concentrations relative to controls. Alternatively, the diagnostic rule is based on the application of a statistical and machine learning algorithm. Such an algorithm uses relationships between effector molecule and disease status observed in training data (with known disease or cell-mediated immunoresponsiveness status) to infer relationships which are then used to predict the status of subjects with unknown status. An algorithm can be employed which provides an index of probability that a subject has a certain level of cell-mediated immunoresponsiveness and/or a disease condition. The algorithm performs a univariate or multivariate analysis function.

Hence, the present invention provides a diagnostic rule based on the application of statistical and machine learning algorithms. Such an algorithm uses the relationships between immune effector molecule and level of cell-mediated immunoresponsiveness or immunosuppression observed in training data (with known immune status) to infer relationships which are then used to predict the status of patients with unknown immune status. Practitioners skilled in the art of data analysis recognize that many different forms of inferring relationships in the training data may be used without materially changing the present invention.

The present invention further contemplates the use of a knowledge base of training data comprising levels of immune effector molecule from a subject with a known cell-mediated immunoresponsiveness level to generate an algorithm which, upon input of a second knowledge base of data comprising levels of the same immune effector molecule from a subject with an unknown immunoresponsiveness level, provides an index of probability that predicts the nature of the cell-mediated immunoresponsiveness.

The term "training data" includes knowledge of levels of immune effector molecule relative to a control wherein the immune effector molecule is determined after exposure of lymphocytes to one or more agents which potentiate the adaptive and innate immune system. A "control" includes a comparison to levels of immune effector molecule in a subject with "normal" immunoresponsiveness or may be a statistically determined level based on trials.

Hence, the term "training data" includes levels of an immune effector molecule.

The levels or concentrations of the immune effector molecule provide the input test data referred to herein as a "second knowledge base of data". The second knowledge base of data either is considered relative to a control or is fed into an algorithm generated by a "first knowledge base of data" which comprise information of the levels of an immune effector in a subject with a known immunological status. The second knowledge base of data is from a subject of unknown status with respect to cell mediated immunoresponsiveness. The output of the algorithm or the comparison to a control is a probability or risk factor, referred to herein as "an index of probability", of a subject having a certain level of immunoresponsiveness or immunosuppressive.

Data generated from the levels of immune effector molecule are input data. The input of data comprising the immune effector levels is compared with a control or is put into the algorithm which provides a risk value of the likelihood that the subject has, for example, an immunosuppressive condition. A treatment regime can also be monitored to ascertain the presence of any immunosuppression. A level of immunosuppression may increase the risk of a subject getting a secondary infection or having a relapse (e.g. during cancer therapy or treatment of a pathogenic infection).

As described above, methods for diagnosing an immunoresponsiveness or immunosuppressive condition by determining the extent to which a subject can mount an adaptive and innate immune response via a level of an immune effector molecule provides a second knowledge base data in an algorithm generated with first knowledge base data or levels of the same effector molecule in subjects with a known immune status. Also provided are methods of detecting immunoresponsiveness comprising determining the presence and/or velocity of an immune effector molecule following stimulation of the adaptive and innate immune system in a subject's sample. By "velocity" it is meant the change in the concentration of the effector molecule in a subject's sample over time.

As indicated above, the term "sample" as used herein means any sample containing an effector molecule following stimulation of adaptive and innate immune process including, but not limited to, biological fluids (including whole blood, plasma, serum, ascites), tissue extracts, freshly harvested cells, and lysates of cells which have been incubated in cell cultures.

The method of the subject invention may be used in the diagnosis and staging of a disease. The present invention may also be used to monitor the progression of a condition and to monitor whether a particular treatment is effective or not. In particular, the method can be used to monitor immunosuppression following surgery, cancer therapy or other or medication or exposure to toxicants.

In an embodiment, the subject invention contemplates a method for monitoring for immunosuppression in a subject, comprising:

(a) providing a sample from a subject;
(b) determining the level of an immune effector molecule following stimulation of adaptive and innate immune processes;

wherein the level of the immune effector relative to a control provides a correlation to the state of cell-mediated immunoresponsiveness and subjecting the levels to an algorithm to provide an index of probability of the subject having a certain level of immunoresponsiveness; and (c) repeating steps (a) and (b) at a later point in time and comparing the result of step (b) with the result of step (c) wherein a difference in the index of probability is indicative of the progression of the condition in the subject.

Reference to an "algorithm" or "algorithmic functions" as outlined above includes the performance of a univariate or multivariate analysis function. A range of different architectures and platforms may be implemented in addition to those described above. It will be appreciated that any form of architecture suitable for implementing the present invention may be used. However, one beneficial technique is the use of distributed architectures. In particular, a number of end stations may be provided at respective geographical locations. This can increase the efficiency of the system by reducing data bandwidth costs and requirements, as well as ensuring that if one base station becomes congested or a fault occurs, other end stations could take over. This also allows load sharing or the like, to ensure access to the system is available at all times.

In this case, it would be necessary to ensure that the base station contains the same information and signature such that different end stations can be used.

It will also be appreciated that in one example, the end stations can be hand-held devices, such as PDAs, mobile phones, or the like, which are capable of transferring the subject data to the base station via a communications network such as the Internet, and receiving the reports.

In the above aspects, the term "data" means the levels or concentrations of the immune effector following potentiation of adaptive and innate immune processes. The "communications network" includes the internet and mobile telephone network and telephone land line. When a server is used, it is generally a client server or more particularly a simple object application protocol (SOAP).

One aspect of the present application includes experiments that demonstrate the cell-mediated immune responsiveness of a subject by measuring responsiveness to particular innate and adaptive immune stimulants. In an embodiment, one or more samples such as a sample of peripheral blood, of enriched white cell fraction of blood or bronchoalveolar lavage may be obtained from a subject having or suspected of development of a particular disease (e.g. autoimmune disease, infection to a pathogenic agent or exposure to beryllium) and the immune responsiveness measured by determination of effector molecules from effector T-cells (e.g. $CD4^+$ T-cells). The assay is conducted in the presence of one or more agents which potentiate the adaptive and innate immune responses.

The immunobinding methods include methods for detecting or quantifying the amount of a reactive component in a sample, which methods require the detection or quantitation of any immune complexes formed during the binding process. Here, one would obtain a sample suspected of containing a cytokine following the co-stimulation of the adaptive and innate immune processes and contacting the sample with an antibody and then detecting or quantifying the amount of immune complexes formed under the specific conditions.

Contacting the chosen biological sample with the antibody under conditions effective and for a period of time sufficient to allow the formation of immune complexes (primary immune complexes) is generally a matter of adding the composition to the sample and incubating the mixture for a period of time long enough for the antibodies to form immune complexes with, i.e. to bind to, any antigens present. After this time, the sample-antibody composition, such as a tissue section, ELISA plate, ELISpot, dot blot or Western blot, will generally be washed to remove any non-specifically bound antibody species, allowing only those antibodies specifically bound within the primary immune complexes to be detected.

In a particular embodiment, the present invention contemplates a method for detecting the presence, absence, level or stage of a disease or condition in a human subject, the method comprising contacting whole blood, which comprises at least 10% of the total volume in a reaction mixture, with one or more agents which potentiate the adaptive and innate immune system and measuring the presence or elevation in the level of an immune effector molecule from T-cells wherein the presence or level of the immune effector molecule is indicative of the disease or condition.

In a further embodiment, the present invention concerns kits for use with the methods described above. In one embodiment, an immunodetection kit is contemplated. In another embodiment, a kit for analysis of a sample from a subject having or suspected of developing a metal or chemically-induced disease is contemplated. In a more particular embodiment, a kit for analysis of a sample from a subject having or suspected of developing a disease is contemplated. In a more particular embodiment, a kit is for assessing the cell-mediated immune responsiveness of a subject before or after a disease state has developed or before or after a subject is given a medicament or is exposed to a toxicant or pollutant. If an antigen is also employed, the kit may also comprise a particular antigen.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of antigen or effector molecule, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of any of the kits will generally include at least one vial, test tube, flask, bottle, syringe or other container means, into which the testing agent, the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

The present invention further contemplates an improved assay to detect a cell-mediated immune response or the level thereof in a subject, the assay comprising incubating a source of lymphocytes from the subject and detecting for the presence or elevation in effector molecules, the improvement comprising further incubating the lymphocytes with one or more agents which potentiate the adaptive and innate immune systems.

The present invention further provides a method of treatment of a subject having a pathogenic infection, an autoimmune disorder or cancer or a propensity for developing such a condition or disorder, the method comprising contacting a source of lymphocytes from the subject with one or more agents which potentiate the adaptive and innate, immune systems and measuring the presence or elevation in the level of an immune effector molecule from T-cells wherein the presence or level of the immune effector molecule is indicative of the level of cell-mediated responsiveness of the subject which is indicative of the presence, absence, level or state of the condition or disorder and then treating the condition or disorder.

The present invention is further described by the following non-limiting Examples.

EXAMPLE 1

Development of Assay

Heparinized blood samples were collected into Li-Hep Vacuette [Registered Trade Mark] tubes (Greiner Bio-one, Germany).

Aliquots of the blood samples were incubated with various concentrations of T-cell receptor agonists: phytohemagglutinin (Cellistis Limited, Australia) anti-human CD3ε antibody (mouse IgG$_1$ clone UCHT1; eBioscience, San Diego), and antibodies to T-cell receptor complex; and Toll-like receptor agonists: Lipomannan TLR-2 ligand (InvivoGen, San Diego), Pam3CSK4 TLR-2 ligand (InvivoGen, San Diego), Poly (I:C) TLR-3 ligand (InvivoGen, San Diego), Lipopolysaccharide TLR-4 ligand (Sigma, Australia), Imidazoquinoline compound—TLR-7/8 ligand, R848 (InvivoGen, San Diego) and CpG oligodeoxynucleotides TLR-9 ligand (Hycult Biotechnology, Netherlands) or saline control in a number of different sized blood collection tubes recommended by the manufacturers of the human Quantiferon [Registered Trade Mark] test (Cellestis Limited, Australia). T-cell receptor-independent stimulants include phorbol myristate acetate (PMA), concanavalnA (ConA) and pokeweek mitogen. Aliquots may be small volumes such as 1 μl to 1000 μl or larger volumes such as 1.5 ml to 200 ml.

In some experiments, glucose was added at various concentrations to the blood before initiation of incubation. In other experiments, two or more stimulants consisting of at least one TCR stimulant and one TLR stimulant were added to blood together in combination.

Stimulated blood samples were incubated for 1 to 48 hours at 37° C., after which plasma was harvested from above the settled blood cells. The amount of IFN-γ present in each plasma sample was then quantified using the Quantiferon-TB [Registered Trade Mark] ELISA (Cellestis Limited, Australia) as per the manufacturer's instructions. Sample IFN-γ was alternatively quantified using the more sensitive Quantiferon-TB Gold [Registered Trade Mark] ELISA (Cellestis Limited, Australia) as per the manufacturer's instructions.

ELISA optical density values for IFN-γ standards run on each ELISA plate were used to construct a standard curve from which the amount of IFN-γ present in each of the test plasma samples was converted to IU/mL values.

EXAMPLE 2

Combinations of T-Cell Receptor (TCR)-Dependent Agonists and Toll-Like Receptor (TLR) Agonists Potential combinations of TCR and TLR agonists used in the assay of Example 1 are shown in Table 3.

TABLE 3

Combinations of TCR and TLR agonists used by the assay

| | TLR agonist | | | | | |
|---|---|---|---|---|---|---|
| TCR agonist | Pam 3CSK4 TLR-2 | Lipomannan (TLR-2) | Poly (I: C)- (TLR-3) | Lipopoly-saccharide (TLR-4) | Imidazo-quinoline (R848) (TLR-7/8) | CpG oligo-nucleotide (TLR-9) |
| PHA (phyto-hemagglutinin) | ✓ | ✓ | ✓ | ✓ | ✓ | ✓ |
| anti-CD3ε antibody | ✓ | ✓ | ✓ | ✓ | ✓ | ✓ |
| Staphylococcal enterotoxinB (SEB) | ✓ | ✓ | ✓ | ✓ | ✓ | ✓ |
| Antibodies to T-cell receptor complex | ✓ | ✓ | ✓ | ✓ | ✓ | ✓ |

EXAMPLE 3

Combination of T-Cell Receptor (TCR)-Independent Agonists and Toll-Like Receptor (TLR) Agonists Potential combinations of TCR-independent agonists and TLR agonists used in the assay of Example 1 are shown in Table 4.

TABLE 4

Combinations of TCR and TLR agonists used by the assay

| | TLR agonist | | | | | |
|---|---|---|---|---|---|---|
| TCR-independent agonists | Pam 3CSK4 TLR-2 | Lipomannan (TLR-2) | Poly (I: C)- (TLR-3) | Lipopoly-saccharide (TLR-4) | Imidazo-quinoline (R848) (TLR-7/8) | CpG oligo-nucleotide (TLR-9) |
| ConA[1] | ✓ | ✓ | ✓ | ✓ | ✓ | ✓ |
| PMA[2] | ✓ | ✓ | ✓ | ✓ | ✓ | ✓ |
| Pokeweed mitogen | ✓ | ✓ | ✓ | ✓ | ✓ | ✓ |

[1] concanavalinA
[2] phorbol myristate acetate

EXAMPLE 4

Assessment of Assay

Figure 1B:
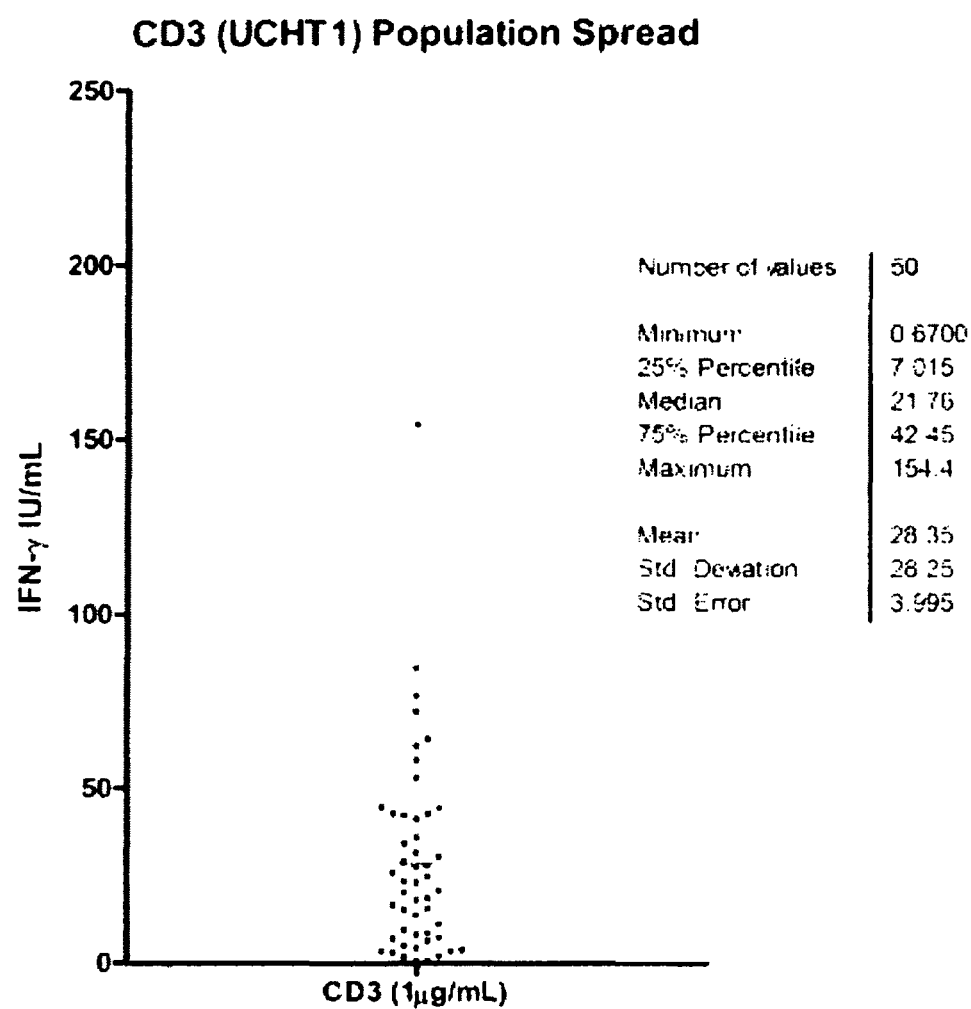
Figure 1C:
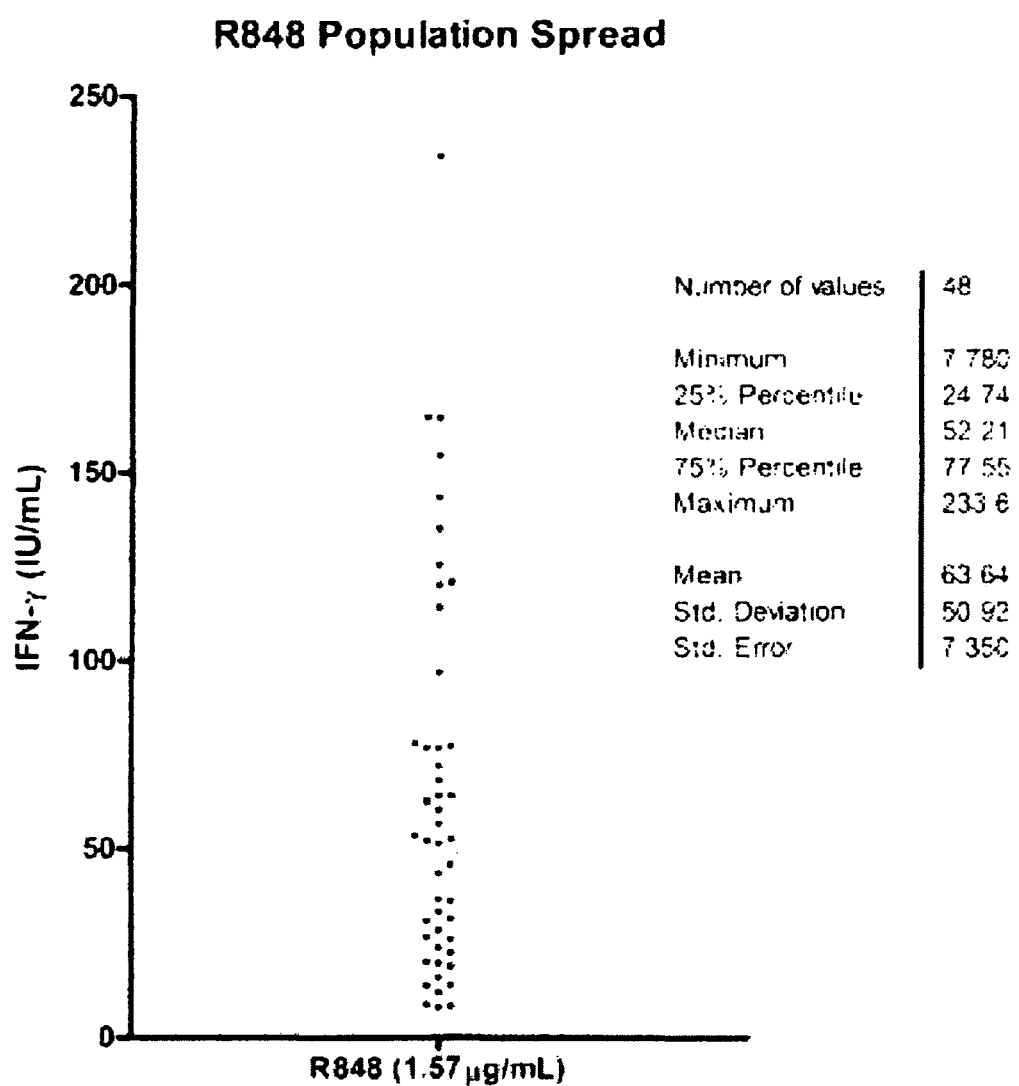
Figure 2A:
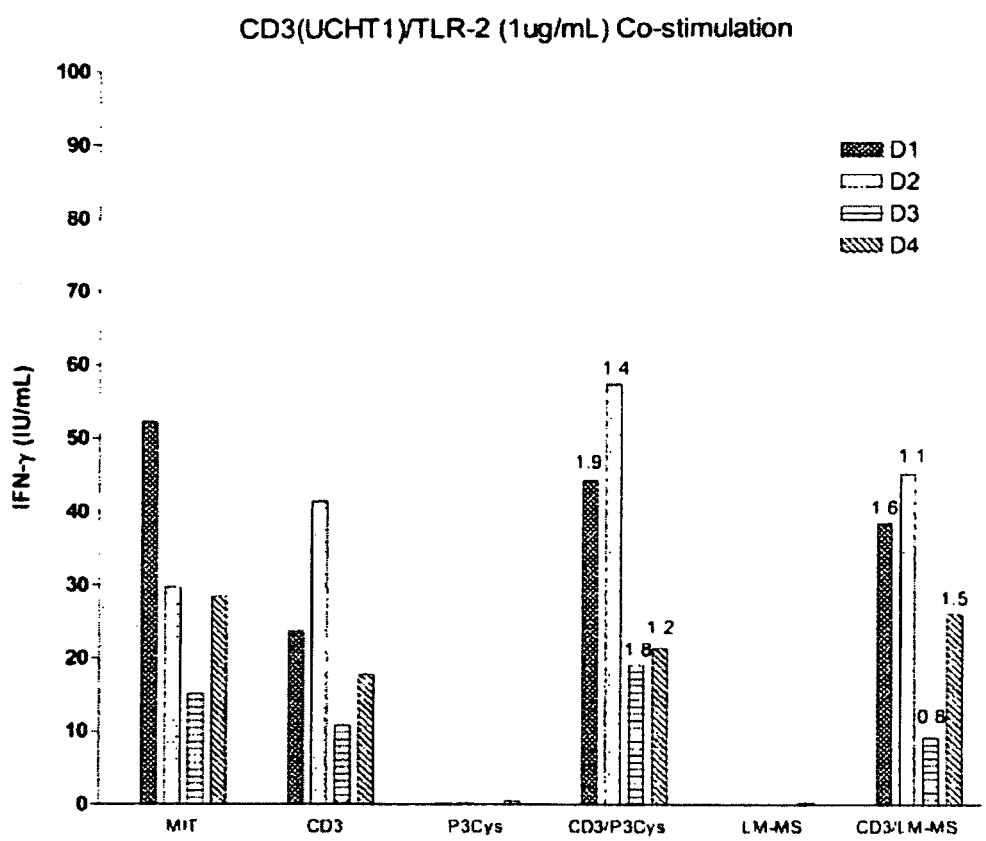
FIGS. 2A through C are graphical representations showing synergy of anti-CD3 antibody (TCR agonist) with various TLR agonists. (A) TLR-2; Pam3CSK4 and lipomannan, (B) TLR-4; LPS (lipopolysaccharide) and (C) TLR-7/8; R848 (imidazoquinoline) compound. Numbers above the graph indicate the fold increase in the IFN-γ response of cultures co-stimulated with a TLR/anti-CD3 antibody versus cultures stimulated with anti-CD3 antibody alone.
Figure 2B:
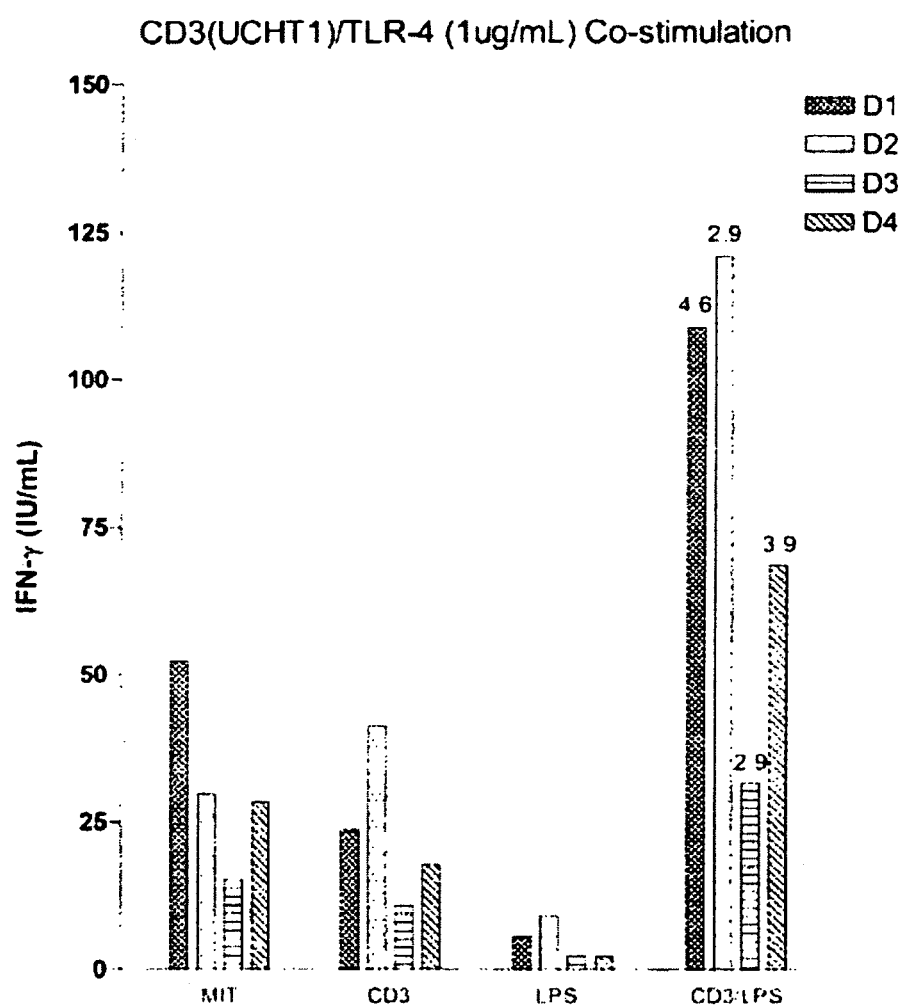
Figure 2C:
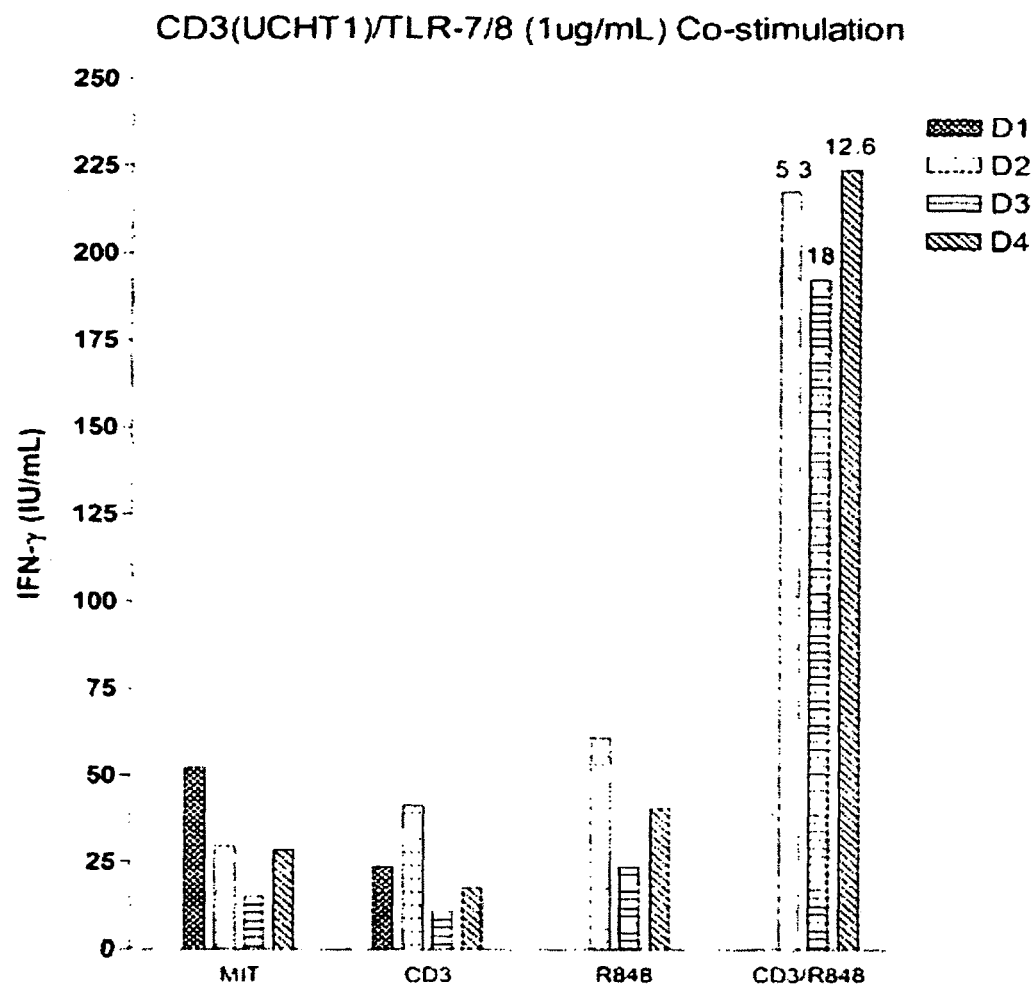
Figure 3:
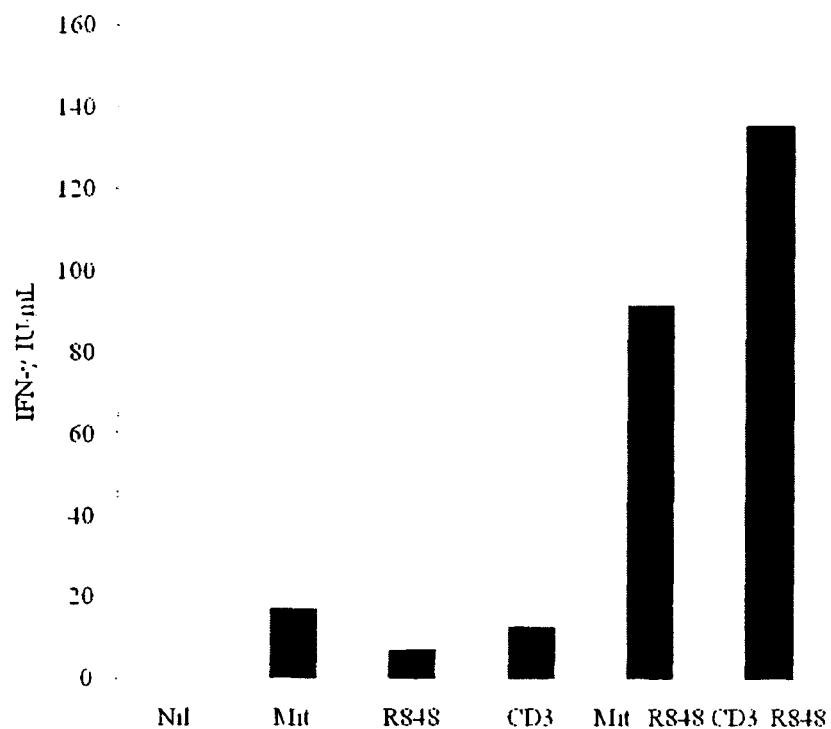
FIG. 3 is a graphical representation of using the synergy of TCR/TLR co-stimulation to set a cut-off (threshold) IFN-γ response in a normal healthy individual. This allows a healthy population reference range to be set resulting in the ability to observe a drop in the IFN-γ response from an immunodeficient individual. Therefore, a measure of immunosuppression due to pharmacological treatment or disease can be assumed if the response falls below the threshold (cut-off) of the healthy population.

The assay involves co-stimulation of T-cell receptor (TCR) and Toll-like receptor (TLR) to assess the combined functional innate and adaptive immunity of an individual. Stimulation of whole blood in vitro with a single stimulant towards TCR or TLR in isolation produces a variable response across healthy donors from extremely high IFN-γ levels to undetectable levels in certain healthy individuals (FIG. 1). For the purposes of setting a healthy reference range and observing a drop in function due to immunodeficiency, a synergy was found that occurs upon combining innate and adaptive immune responses (FIG. 2). Dual stimulation potentiates responses elevating the normal healthy population mean allowing a cut-off level to be determined (FIG. 3). An elevated normal healthy population mean also allows one to observe a drop in the IFN-γ response from an immunodeficient individual. Therefore, a measure of immunosuppression due to pharmacological treatment or disease can be assumed if the response falls below the threshold (cut-off) of the healthy population.

EXAMPLE 5

Use of T-Cell Receptor Agonist

This Example provides a method of assessing combined innate and adaptive immunity in vitro using a toll-like receptor (TLR) agonist (imidazoquinoline compound, R848 that is specific for NK cells) and a T-cell receptor (TCR) agonist for co-stimulation of immune cells. This in vitro diagnostic is for use with whole blood, peripheral blood mononuclear cells (PBMCs) and purified cell populations with feeder layers. However, other TLR agonists specific for different cell types of the immune system could also be included.

The QFN in-tube technology (Cellestis) provides a method for measuring cell mediated immunity (CMI) following stimulation of whole blood with a combination of stimulants that specifically activate distinct immune cells. The stimulation is carried out in a closed vessel that is incubated for 24 hours at 37° C. without humidification. Plasma is harvested from the whole blood and IFN-γ is detected using a one-step ELISA, providing a measure of target cell function. Specifically, the assay measures the functional immune status of individuals by assessing the combinatorial innate (NK cell) and adaptive (T cell) immune response. The test is used to monitor the general immune status of an individual for in vitro diagnostic and prognostic applications.

The device measures the total IFN-γ output produced in response to a combination of two stimulants provided simultaneously. The resulting "value" refers to the net functional immune state of an individual at a given point in time. This allows for longitudinal and latitudinal comparison of immune state.

Data indicate that the following order, TLR-7/8>TLR-4>TLR-3>TLR-2 represents the decreasing effectiveness of TLR class of agonists that exert a synergistic response when used in combination with anti-CD3 antibody (TCR agonist) for the purpose of developing a diagnostic assay with clinical utility. In this Example, therefore, TLR-7/8 agonist is used such as an imidazoquinoline compound (R848) to obtain a maximal synergistic response. However, different applications may require the use of sub-maximal synergy or indeed the use of two or more combinations of TLR classes with a TCR agonist such as anti-CD3 antibody or mitogen (phytohemagglutinin; PHA). It is shown that in the diagnostic assay, mitogen exerts its function via the TCR located on T-cells. This is evidenced by the ability of anti-CD3 antibody to abrogate the mitogen response when both stimulants are used in combination.

EXAMPLE 6

Determination of Immunosuppression in Subjects on Medicaments

The assay is conducted on subjects exposed to medicaments such as chemotherapeutic agents or agents used to treat rheumatoid arthritis, cancer or inflammatory bowel disease. In subjects where immunosuppression is identified, care is taken to avoid secondary infections. For example, antibiotics may be provided or immunostimulants.

EXAMPLE 7

Stimulation of Whole Blood with TCR Agonist and TLR Agonist

Whole blood was stimulated with a combination of anti-CD3 antibody (TCR agonist) and the TLR-7/8 agonist; R848 (imidazoquinoline). The observed levels of Monokine induced by Gamma interferon (MIG; CXCL9) and IFN-γ are shown in Table 5. Values are shown with the corresponding background control subtracted (NIL). The data show that MIG and IFN-γ correspond as indicators of stimulation.

TABLE 5

| Subject | MIG (CXCL9) pg/mL | IFN-γ pg/mL |
| --- | --- | --- |
| 1 | >2000 | 34280 |
| 2 | 1567 | 20040 |
| 3 | 1494 | 20000 |
| 4 | >2000 | 31680 |
| 5 | >2000 | 35320 |
| 6 | >2000 | 73760 |
| 7 | 1744 | 25400 |
| 8 | >2000 | 24840 |

Whole blood was also stimulated with or without a combination of anti-CD3 antibody (TCR agonist) and the TLR-7/8 agonist; R848 (imidazoquinoline). The resulting plasma was used to profile known cytokines, chemokines and extracellular signaling molecules. Targets detected could be used singularly or in combination with other effectors as reporter molecules. This is particularly useful for multiplexing. The targets detected are shown in Table 6.

TABLE 6

| Targets |
| --- |
| Complement Component 5a (C5a) |
| Gro α (CXCL1) |
| sICAM-1 (CD54) |
| IFN-γ (Type II IFN) |
| IL-1α (IL-1F1) |
| IL-1β (IL-1F2) |
| IL-1ra (IL-1F3) |
| IL-6 |
| IL-8 (CXCL8) |
| IL-10 |
| IL-16 (LCF) |
| IL-17 |
| IP-10 (CXCL10) |
| I-TAC (CXCL11) |
| MCP-1 (CCL2) |
| MIF (GIF) |
| MIP-1α (CCL3) |
| MIP-1β (CCL4) |
| Serpin E1 (PAI-1) |
| RANTES (CCL5) |
| TNF-α (TNFSF2) |
| MIG (CXCL9) |

TABLE 7

| | HIV + ve Untreated (TCR) | HIV + ve Unreated (TLR) | HIV + ve Untreated (TCR + TLR) | Healthy Normal (TCR) | Healthy Normal (TLR) | Healthy Normal (TCR + TLR) |
| --- | --- | --- | --- | --- | --- | --- |
| Number of values | 24 | 24 | 24 | 50 | 49 | 50 |

TABLE 7-continued

|  | HIV + ve Untreated (TCR) | HIV + ve Unreated (TLR) | HIV + ve Untreated (TCR + TLR) | Healthy Normal (TCR) | Healthy Normal (TLR) | Healthy Normal (TCR + TLR) |
| --- | --- | --- | --- | --- | --- | --- |
| Minimum | 0.935 | 0 | 2.65 | 0.67 | 7.78 | 34.17 |
| 25% Percentile | 26.63 | 1.601 | 54.35 | 7.068 | 24.74 | 232.1 |
| Median | 77.45 | 6.675 | 91.28 | 21.76 | 52.43 | 554 |
| 75% Percentile | 108.6 | 22.41 | 291.5 | 42.39 | 87.33 | 882.5 |
| Maximum | 331 | 122 | 1349 | 154.4 | 439.1 | 1989 |

Figure 4:
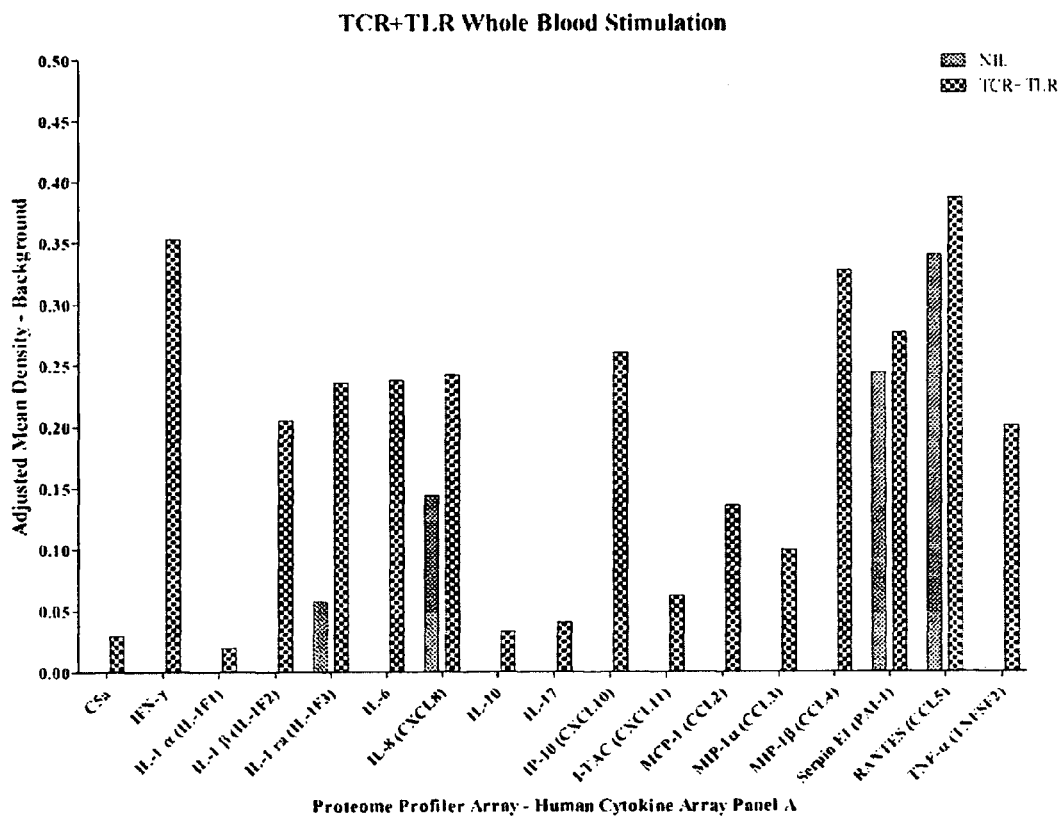
FIG. 4 is a graphical representation showing detection of multiple analytes in human plasma from treated (TCR+TLR agonists) and untreated (NIL) whole blood. Human whole blood was treated by stimulating with a combination of anti-CD3 antibody (TCR agonist) and the TLR-7/8 agonist; R848 (imidazoquinoline). Several chemokines, cytokines and extracellular signaling molecules are only found in the plasma of whole blood stimulated with a TCR and TLR agonist simultaneously (Blue bars; TCR+TLR). Several other molecules are up-regulated as compared with untreated whole blood (red bars; NIL).

The resulting profile of cytokines, chemokines and extracellular signaling molecules is represented graphically in FIG. 4. Several cytokines, chemokines and extracellular signaling molecules were only found in plasma of whole blood stimulated with a TCR and TLR agonist simultaneously (blue bars, TCR+TLR). Several others were up-regulated as compared with untreated whole blood (red bars, NIL).

Figure 5:
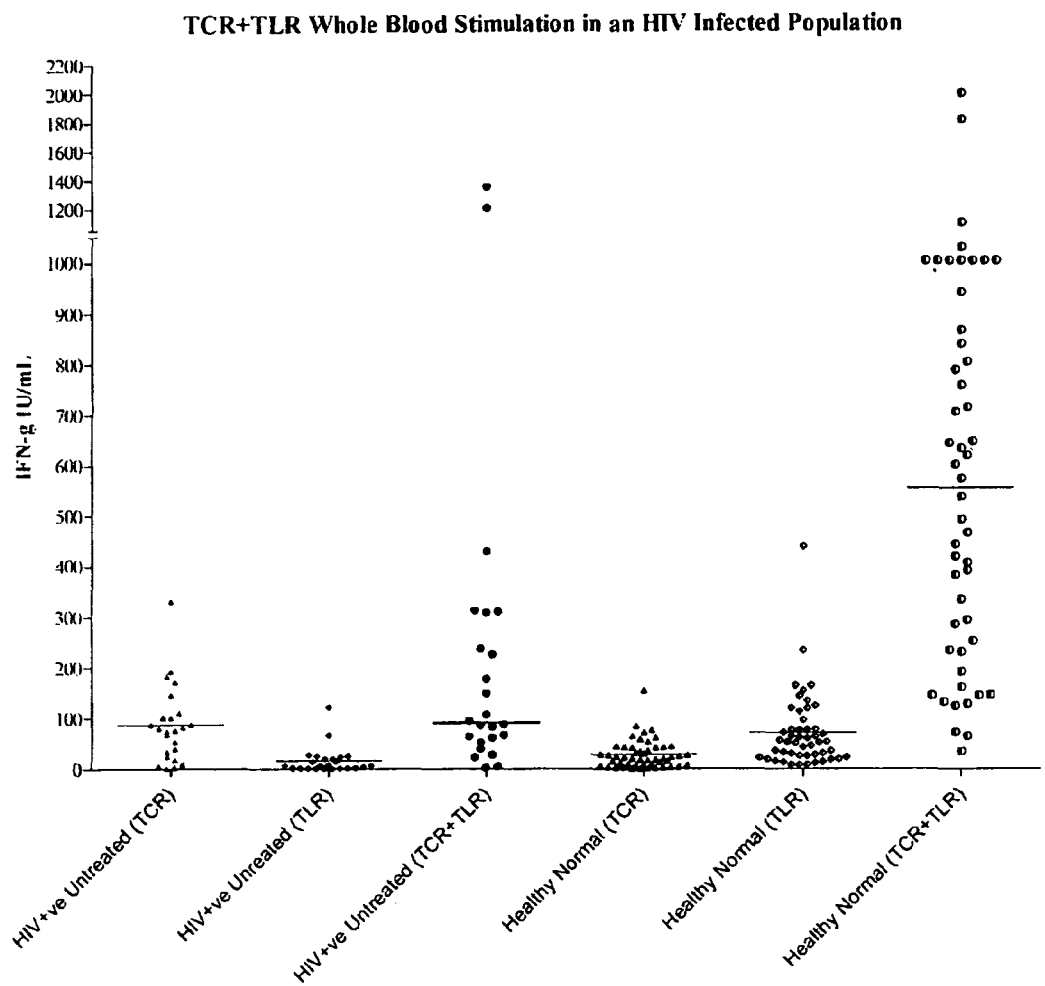
FIG. 5 is a graphical representation of the synergy observed between dual stimulant (TCR+TLR) IFN-γ responses from whole blood cultures as compared with stimulation of whole blood with either a TCR agonist or TLR agonist alone in an HIV infected and normal healthy cohort. Study populations include (i) untreated HIV positive (sourced from South Africa); and (ii) normal healthy donors (sourced from Australia). Population medians are shown in Table 7.

The synergy observed between dual stimulation with TCR and TLR agonists on IFN-γ responses from whole blood cultures compared to stimulation of whole blood with either a TCR agonist or TLR agonist alone is shown in FIG. 5.

The population tested were an HIV infected cohort and a normal healthy cohort. Study populations include (i) untreated HIV positive (sourced from South Africa); and (ii) normal healthy donors (sourced from Australia). Population medians are shown in Table 7.

Figure 6:
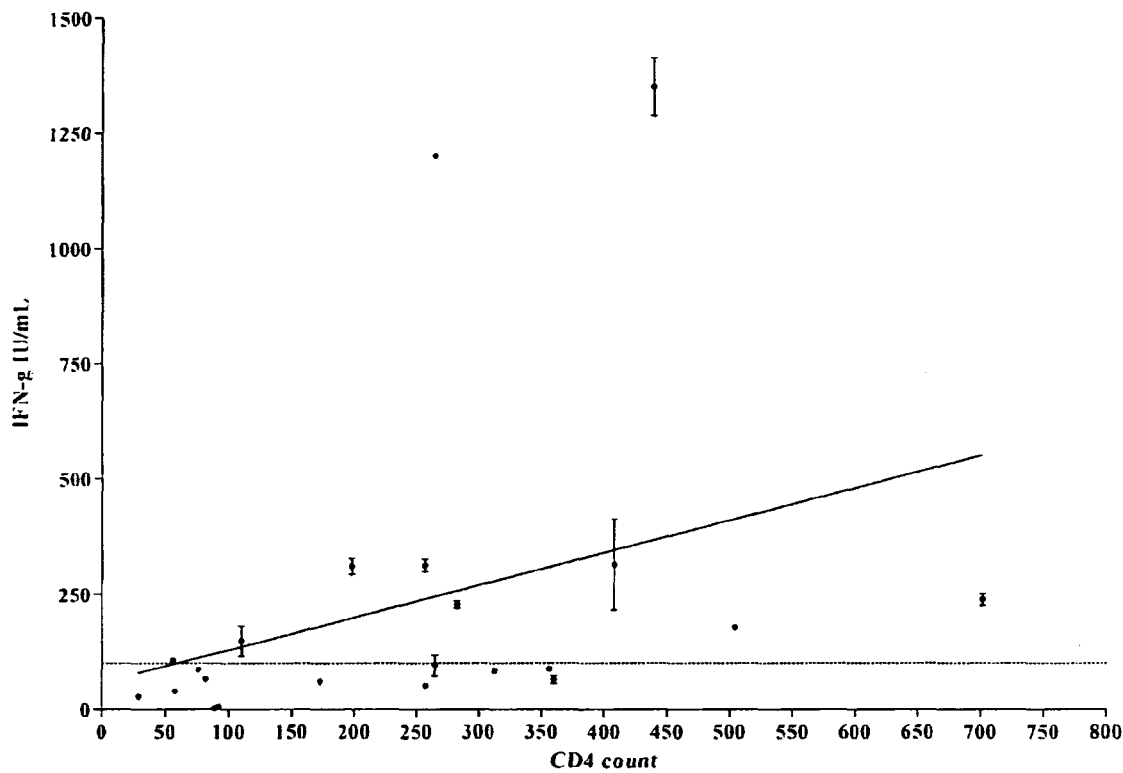
FIG. 6 is a graphical representation of the correlation observed between the IFN-γ response level and CD4 T-cell count observed in combined agonist (TCR+TLR) stimulated whole blood of an HIV infected cohort.

A correlation between IFN-γ response level and CD4 T-cell count following TCR+TLR co-stimulation is shown in FIG. 6. Whole blood from an HIV infected cohort was stimulated.

Figure 7:
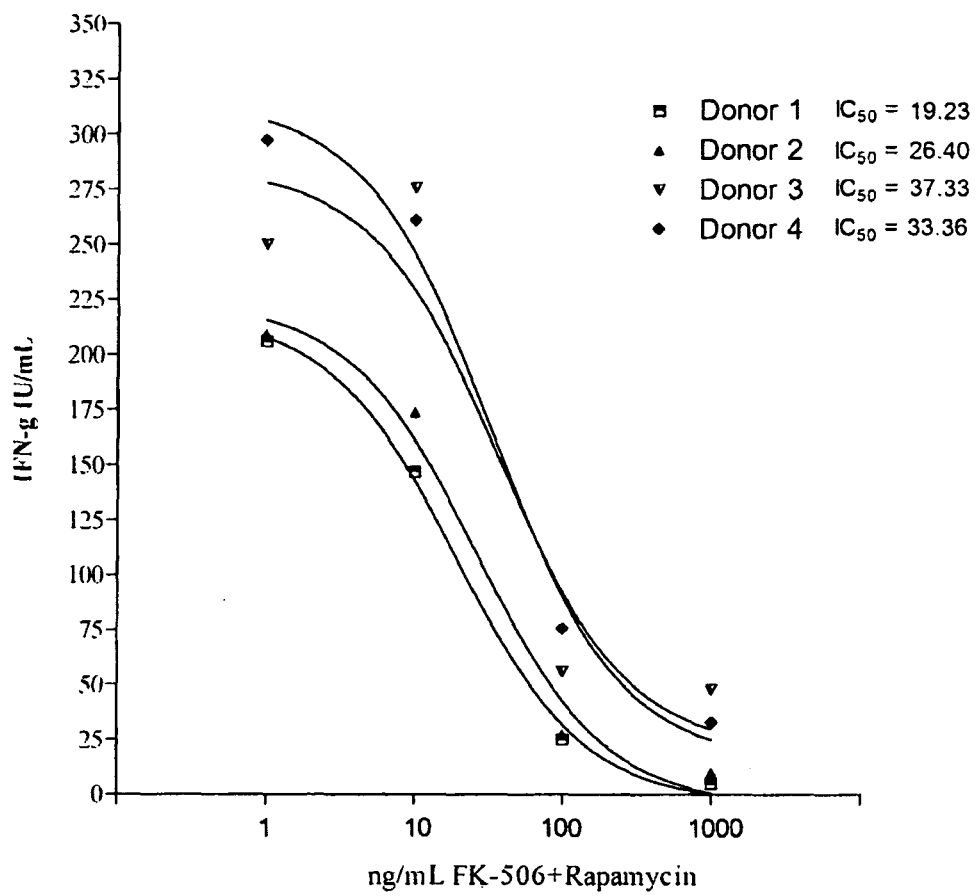
FIG. 7 is a graphical representation showing the stimulation of whole blood with a combination of TCR and TLR agonists which allows the determination of immunosuppressant inhibitory concentration in a given donor.

The stimulation of whole blood with a combination of TCR and TLR agonists also allows determination of immunosuppressant inhibitory concentration in a given donor (FIG. 7).

Those skilled in the art will appreciate that the invention described herein is susceptible to variations and modifications other than those specifically described, and that a range of agents effect T-cell receptor-dependent and -independent potentiation and Toll-like receptor potentiation or a combination of both. It is to be understood that the invention includes all such agents. The invention also includes all of the steps, features, compositions and compounds referred to or indicated in this specification, individually or collectively, and any and all combinations of any two or more of said steps or features.

BIBLIOGRAPHY

Biggs et al, Cytometry 36:36-45, 1999
Chang et al, J. Virol. 83:7649-58, 2009
Cooper et al, Hematology:314-30, 2003
Daneshvar et al, J. Immunol. Methods 226(1-2):119-128, 1999
Douek et al, Annu. Rev. Med. 60:471-84, 2009
Dung et al, J. Raman Spectrosc. 24(5):281-285, 1993
Eriksson et al, Biophys. J. 2:64, 1993
Fu et al, Nature Biotechnology 17:1109-1111, 1999
Hengel and Kovacs, J. Infect. Dis. 188(12):1791-3, 2003
Hu and Gatti, Curr Opin Allergy Clin Immunol. 8(6):540-546, 2008
Kowalski et al, J Immunotoxicol. 4(3):225-32, 2007
Lakowicz et al, Biophys. J. 72:567, 1997
Lewis et al, Dyes Pigm. 42(2):197, 1999
Malemed et al, "Flow cytometry and sorting", $2^{nd}$ Ed., New York, Wiley-Liss; 1990
Matesanz et al, Transplant Proc. 41(6):2297-301, 2009
Nowroozalizadeh et al, Cytokine 46:325-31, 2009
Rahman et al, J. Org. Chem. 63:6196, 1998
Rapaport et al, Appl. Phys. Lett. 74(3):329-331, 1999
Schrem et al, Dtsch Arztebl Int. 106(9):148-156, 2009
Solomon et al, J. Infect. Dis. 187:1915-23, 2003
Tawa et al, Mater. Res. Soc. Symp. Proc. 488 [Electrical, Optical and Magnetic Properties of Organic Solid-State Materials IV], 885-890
Youvan et al., Biotechnology et elia 3:1-18, 1997

The invention claimed is:

1. An in vitro method for determining immunoresponsiveness or immunosuppression in lymphocytes that are present in a sample source of lymphocytes obtained from a test subject, comprising:
   (i) contacting in vitro in a blood collection tube a sample source of lymphocytes obtained from the test subject with at least two agents which potentiate adaptive and innate immune systems to exert a synergistic response in vitro, wherein the lymphocytes comprise T-lymphocytes and NK-lymphocytes and wherein the at least two agents comprise at least one adaptive immune stimulant that stimulates the T-lymphocytes and is selected from a T-cell receptor agonist and a T-cell receptor-independent T-cell stimulant, and at least one TLR agonist that stimulates the NK-lymphyocytes;
   (ii) measuring a first level of at least one immune effector molecule produced by immune cells that are present in the sample source of lymphocytes following said step of contacting, said immune effector molecule being selected from complement component C5a, Groα (CXCL1), sICAM-1 (CD54), IFN-γ (Type II IFN), IL-1α (IL-1F1), IL-1β (IL-1F2), IL-1ra (IL-1F3), IL-6, IL-8 (CXCL8), IL-10, IL-16 (LCF), IL-17, IP-10 (CXCL10), I-TAC (CXCL11), MCP-1 (CCL2), MIF (GIF), MIP-1α (CCL3), MIP-1β (CCL4), Serpin E1 (PAI-1), RANTES (CCL5), TNF-α (TNFSF2), and MIG (CXCL9); and
   (iii) comparing the first level measured in (ii) to a control level of said at least one immune effector molecule that is produced by control immune cells following contact with the at least two agents which potentiate adaptive and innate immune systems, said control immune cells being present in a control sample source that contains control lymphocytes and that has been obtained from a control subject known to have normal cell-mediated immune response activity, and therefrom determining immunoresponsiveness or immunosuppression in the lymphocytes that are present in the sample source of lymphocytes.

2. The method of claim 1 wherein the subject is a human.

3. The method of claim 1 wherein the sample comprises whole blood undiluted.

4. The method of claim 3 wherein the sample is selected from (a) whole blood which comprises from about 10% to 100% by volume of the sample to be assayed, (b) whole blood which comprises from about 50% to 100% by volume of the sample to be assayed and (c) whole blood which comprises from about 80% to 100% by volume of the sample to be assayed.

5. The method of claim 1 wherein the sample source of lymphocytes is a small blood volume of from 1 µl to 1000 µl.

6. The method of claim 1 wherein the sample source of lymphocytes is whole blood and the step of contacting further comprises incubating the lymphocytes with an antigen.

7. The method of claim 1 wherein the sample source of lymphocytes is whole blood that is collected in a tube comprising heparin.

8. The method of claim 1 wherein the adaptive immune stimulant is a T-cell receptor agonist.

9. The method of claim 1 wherein the adaptive immune stimulant is selected from a CpG oligonucleotide, antibodies to a T-cell receptor complex, phytohemagglutinin and anti-CD3 antibody.

10. The method of claim 1 wherein the agent which potentiates the innate immune system is a Toll-like receptor (TLR) agonist.

11. The method of claim 10 wherein the TLR agonist stimulates via TLR-7/8, TLR-4, TLR-3 or TLR-2.

12. The method of claim 11 wherein the agonist is selected from a TLR ligand, lipomannan, poly (I:C)-, and a imidazoquinoline, R848.

13. The method of claim 1 wherein the agent which potentiates the adaptive immune system does not stimulate via a T-cell receptor.

14. The method of claim 13 wherein the agent is selected from concanavalinA, pokeweed mitogen and phorbol myristate acetate (PMA).

15. The method of claim 1 wherein the immune effector molecule is selected from IFN-γ, IL-1α, IL-1β, IL-6, IL-8, IL-10, IL-16 and IL-17.

16. The method of claim 15 wherein the immune effector molecule is IFN-γ.

17. The method of claim 1 wherein the immune effectors are detected with specific antibodies.

18. The method of claim 17 wherein the immune effectors are detected either by ELISA or by ELISpot.

19. The method of claim 1 wherein the subject has an infection by a pathogenic agent selected from *Mycobacterium* species, *Staphylococcus* species, *Streptococcus* species, *Borrelia* species, *Escherichia coli, Salmonella* species, *Clostridium* species, *Shigella* species, *Proteus* species, *Bacillus* species, Herpes virus, Hepatitis B or C virus and Human immune deficiency virus (HIV) or a disease or disease condition resulting therefrom.

20. The method of claim 19 wherein the disease condition is an infection by *Mycobacterium tuberculosis* or tuberculosis (TB).

21. The method of claim 19 wherein the disease condition is infection by a hepatitis virus or HIV.

22. The method of claim 19 wherein the subject has a disease condition selected from alopecia areata, ankylosing spondylitis, antiphospholipid syndrome, autoimmune Addison's disease multiple sclerosis, autoimmune disease of the adrenal gland, autoimmune hemolytic anemia, autoimmune hepatitis, autoimmune oophoritis and orchitis, Behcet's disease, bullous pemphigoid, cardiomyopathy, celiac sprue-dermatitis, chronic fatigue syndrome (CFIDS), chronic inflammatory demyelinating, chronic inflammatory polyneuropathy, Churg-Strauss syndrome, cicatricial pemphigoid, crest syndrome, cold agglutinin disease, Crohn's disease, dermatitis herpetiformis, discoid lupus, essential mixed cryoglobulinemia, fibromyalgia, glomerulonephritis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), lichen planus, lupus, Meniere's disease, mixed connective tissue disease, multiple sclerosis, myasthenia gravis, myocarditis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arrthritis, sarcoidosis, scleroderma, Sjogren's syndrome, stiff-man syndrome, systemic lupus erythematosus, Takayasu arteritis, temporal arteritis/giant cell arteritis, ulcerative colitis, uveitis, vasculitis, vitiligo and inflammatory bowel disease.

23. The method of claim 22 wherein the disease is Celiac's disease.

24. The method of claim 22 wherein the disease is autoimmune diabetes.

25. The method of claim 1 wherein the subject has a cancer selected from ABL1 protooncogene, AIDS related cancers, acoustic neuroma, acute lymphocytic leukaemia, acute myeloid leukaemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukaemia, childhood soft tissue sarcoma, chondrosarcoma, choriocarcinoma, chronic lymphocytic leukaemia, chronic myeloid leukaemia, colorectal cancers, cutaneous T-Cell lymphoma, dermatofibrosarcoma-protuberans, desmoplastic-small-round-cell-tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynaecological cancers, hematological malignancies, hairy cell leukaemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's-cell-histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid-tumor-of-kidney, medulloblastoma, melanoma, merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, nijmegen breakage syndrome, non-melanoma skin cancer, non-small-cell-lung-cancer-(NSCLC), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumors, pituitary cancer, polycythemia vera, prostate cancer, rare-cancers-and-associated-disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia and Wilms' tumor.

\* \* \* \* \*

UNITED STATES PATENT AND TRADEMARK OFFICE
CERTIFICATE OF CORRECTION

PATENT NO. : 9,459,253 B2  Page 1 of 1
APPLICATION NO. : 13/516150
DATED : October 4, 2016
INVENTOR(S) : Jeff Boyle et al.

It is certified that error appears in the above-identified patent and that said Letters Patent is hereby corrected as shown below:

In the Claims

Column 33, Line 41:
"molecule is selected from IFN-γ,IL-1α, IL-1β, IL-6, IL-8," should read, --molecule is selected from IFN-γ, IL-1α, IL-1β, IL-6, IL-8,--.

Signed and Sealed this
Fourth Day of April, 2017

Michelle K. Lee
*Director of the United States Patent and Trademark Office*